US009410160B2

(12) United States Patent
Zheng et al.

(10) Patent No.: US 9,410,160 B2
(45) Date of Patent: Aug. 9, 2016

(54) PLANT SNF1-RELATED PROTEIN KINASE GENE

(75) Inventors: Zhifu Zheng, Indianapolis, IN (US); Thomas W. Greene, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 258 days.

(21) Appl. No.: 12/757,696

(22) Filed: Apr. 9, 2010

(65) Prior Publication Data

US 2010/0281574 A1 Nov. 4, 2010

Related U.S. Application Data

(60) Provisional application No. 61/168,532, filed on Apr. 10, 2009.

(51) Int. Cl.
*C12N 15/82* (2006.01)
*C12N 5/14* (2006.01)
*C12N 9/12* (2006.01)

(52) U.S. Cl.
CPC .......... *C12N 15/8247* (2013.01); *C12N 9/1205* (2013.01); *C12N 15/8245* (2013.01); *C12N 15/8261* (2013.01); *C12N 15/8273* (2013.01)

(58) Field of Classification Search
None
See application file for complete search history.

(56) References Cited

U.S. PATENT DOCUMENTS

| | | | | |
|---|---|---|---|---|
| 5,952,544 | A * | 9/1999 | Browse et al. | 800/295 |
| 7,196,245 | B2 * | 3/2007 | Jiang et al. | 800/278 |
| 7,230,160 | B2 * | 6/2007 | Benning et al. | 800/281 |
| 7,273,966 | B2 | 9/2007 | Voelker et al. | |
| 7,371,941 | B2 * | 5/2008 | Pylman et al. | 800/320.1 |
| 7,714,189 | B2 * | 5/2010 | Manjunath et al. | 800/288 |
| 7,989,678 | B2 * | 8/2011 | Mankin et al. | 800/294 |
| 2006/0150283 | A1 | 7/2006 | Alexandrov et al. | |
| 2007/0214517 | A1 * | 9/2007 | Alexandrov et al. | 800/278 |
| 2011/0167515 | A1 | 7/2011 | Zheng et al. | |

FOREIGN PATENT DOCUMENTS

| | | |
|---|---|---|
| WO | WO00/53746 | 9/2000 |
| WO | WO2006/008271 | 1/2006 |
| WO | 2008122980 A2 | 10/2008 |

OTHER PUBLICATIONS

Mustilli et al, The Plant Cell, Dec. 2002, vol. 14, pp. 3089-3099.*
Shin et al, PNAS, Apr. 10, 2007, vol. 104, No. 15, pp. 6460-6465.*
Umezawa et al, The Plant Cell, Dec. 2002, vol. 14, pp. 3089-3099.*
Umezawa et al, Current Opinion in Biotechnology, 2006, Vo. 17, pp. 113-122.*
Sjolander 2004 Bioinformatics 20:2 p. 170-179.*
Miao et al 2006 (The Plant Cell 18: p. 2749-2766).*
Ma and Wu 2007 (Plant Molecular Biology 65: p. 511-518).*
Gonzalez-Ballester, David et al., The central role of a SNRK2 kinase in sulfur deprivation responses1[W][OA], Plant Physiology, May 2008, pp. 216-227, vol. 147.
International Search Report for PCT/US2010/030563, mailed Jan. 24, 2011.
Written Opinion for PCT/US2010/030563, mailed Jan. 24, 2011.
Umezawa et al., SRK2C, a SNF1-related protein kinase 2, improves drought tolerance by controlling stress-responsive gene expression in *Arabidopsis thaliana*, PNAS, Dec. 7, 2004, pp. 17306-17311, vol. 101, No. 49.
GenBank accession No. AY081538, GI: 20148418 (Apr. 14, 2002).
Xu et al., "Expression activity of maize Ubi-1 promoter in fertile transgenic maize plants," Shi Yan Sheng Wu Xue Bao, Dec. 2002, vol. 35, No. 4 pp. 296-302 (abstract only).
Belin, C., et al. "Identification of Features Regulating OST1 Kinase Activity and OSTI Function in Guard Cells1[W]", Plant Physiology, Aug. 2006, pp. 1316-1327, vol. 141.
Hrabak E. M., et al. "The *arabidopsis* CDPK-SnRK superfamily of protein kinases", Plant Physiology, Jun. 2003, pp. 666-680, vol. 132.
Ky, Huynh et al, "Sequence and Expression Analysis of EgSAPK, a Putative Member of the Serine/Threonine Protein Kinases in Oil Palm (Elaeis guineensis Jacq.)", International Journal of Botany, 2009, pp. 76-84, vol. 5, No. 1.
Jain, Mukesh et al., "Cloning and expression analyses of sucrose non-fermenting-1-related kinase 1 (SnRK1b) gene during development of sorghum and maize endosperm and its implicated role in sugar-to-starch metabolic transition", Physiologia Plantarum, 2008, pp. 161-173, vol. 134.
Yoshida, Riichiro et al. "ABA-activated SnRK2 protein kinase is required for dehydration stress signaling in Arabidopsis", Plant and Cell Physiology, 2002, pp. 1473-1483, vol. 43, No. 12.
Yoshida, R., et al, "The Regulatory Domain of SRK2E/OST1/SnRK2.6 Interacts with ABI1 and Integrates Abscisic Acid (ABA) and Osmotic Stress Signals Controlling Stomatal Closure in *Arabidopsis*", Journal of Biological Chemistry, Feb. 24, 2006, pp. 5310-5318, vol. 281, No. 8.
Zheng, Z. et al., "The Protein Kinase SnRK2.6 Mediates the Regulation of Sucrose Metabolism and Plant Growth in *Arabidopsis*", Plant Physiology, May 2010, pp. 99-113, vol. 153.

(Continued)

*Primary Examiner* — Brent Page
*Assistant Examiner* — Matthew Keogh
(74) *Attorney, Agent, or Firm* — C. Philip Poirier; Magleby Cataxinos & Greenwod

(57) ABSTRACT

The present invention relates to the isolation, purification, characterization and use of the plant Snf1-related protein kinase (SnRK) gene and genetic products. The invention includes isolated and purified SnRK DNA and relates to methods of regulating water loss and plant drought tolerance, sucrose content, starch content, seed oil content, fatty acid synthesis, seed oil acyl composition, seed size/weight, resistance/tolerance to biotic stresses, increased root biomass, and/or carbon flux into other seed components, plant, using the gene, and to tissues and plants transformed with the gene. The invention also relates to transgenic plants, plant tissues and plant seeds having a genome containing an introduced DNA sequence of the invention, and a method of producing such plants and plant seeds.

34 Claims, 7 Drawing Sheets

(56) References Cited

OTHER PUBLICATIONS

Tiessen et al., Evidence that SNF1-related kinase and hexokinase are involved in separate sugar-signalling pathways modulating post-translational redox activation of ADP-glucose pyrophosphorylase in potato tubers, The Plant Journal, (2003), 490-500.

Boudsocq et al., Mechanisms of Signal Transduction: Identification of Nine Sucrose 1-related Protein Kinases 2 Activated by Hypersmotic and Saline Stresses in *Arabidopsis thaliana*, The Journal of Biological Chemistry, Jul. 29, 2004, vol. 279, No. 40, The American Society for Biochemistry and Molecular Biology, Inc., pp. 41758-41766.

International Preliminary Report on Patentability and Written Opinion for PCT/US2010/030563, mailed Oct. 11, 2011, 6 pages.

Kobayashi et al., Differential Activation of the Rice Sucrose Nonfermenting1-Related Protein Kinase2 Family by Hyperosmotic Stress and Abscisic Acid, The Plant Cell, May 2004, vol. 16, American Society of Plant Biologists, pp. 1163-1177.

Rooke et al., Marker gene expression driven by the maize ubiquitin promoter in trangenic wheat, Annals of Applied Biology, Jan. 18, 2000, vol. 136, Association of Applied Biologists, pp. 167-172.

Rooke et al. 2000 Annals of Applied Biology 136: p. 167-172.

Boshoff et al., "Purification, Gene Cloning, Targeted Knockout, Overexpression, and Biochemical Characterization of the Major Pyrazinamidase from *Mycobacterium smegmatis*," Journal of Bacteriology, Nov. 1998, p. 5809-5814.

Davis et al., Metallothionein Expression Protects against Carbon Tetrachloride-Induced Hepatotoxicity, but Overexpression and Dietary Zinc Supplementation Provide No Further Protection in Metallothionein Transgenic and Knockout Mice, American Society for Nutritional Sciences, 2001, pp. 215-222.

Lin, Yanling, The effect of SOD-2 knockout and overexpression on brain injury after ischemia and reperfusion in hyperglycemic mice, <http://hdl.handle.net/10125/20745> 2007, 2 pages.

Markovtsov et al, "Antiproliferative effect of BRCA1-associated protein 1 (BAP1) knockout and overexpression on tumor cell lines," Proc Amer Assoc Cancer Res, vol. 45, 2004, 1 page abstract.

* cited by examiner

PLANT SNF1-RELATED PROTEIN KINASE GENE

CROSS-REFERENCE TO RELATED APPLICATION

This application claims the benefit of the filing date of U.S. Provisional Patent Application Ser. No. 61/168,532, filed Apr. 10, 2009, for "PLANT SNF1-RELATED PROTEIN KINASE GENE."

TECHNICAL FIELD

This invention relates generally to plant genes useful for the genetic manipulation of plant characteristics. More specifically, the invention relates to the identification, isolation and introduction of Snf1-related protein kinase (SnRK) genes useful, for example, for altering plant water loss and plant drought tolerance, sucrose content, starch content, seed oil content, fatty acid synthesis, seed oil acyl composition, seed size/weight, resistance/tolerance to biotic stresses, increased biomass, and/or carbon flux into other seed components, in commercial or crop plants.

BACKGROUND

A large body of evidence demonstrates that the Snf1-related protein kinases serve as important regulators modulating fundamental metabolic pathways in response to nutritional and environmental stresses in yeast and mammalian cells (Hardie, 2007; Hardie and Carling, 1997; Hedbacker and Carlson, 2008). In the yeast *Saccharomyces cerevisiae*, the sucrose non-fermenting kinase Snf1 is a serine/threonine protein kinase that is required for derepression of the transcription of glucose-repressible genes. It is also involved in gluconeogenesis, glycogen accumulation, mitochondrial and peroxisome biogenesis, and sporulation. The mammalian ortholog of the yeast Snf1 is the adenosine monophosphate (AMP)-activated protein kinase (AMPK).

Upon cellular stress responses that deplete ATP, AMPK is activated and thus phosphorylates and inhibits the enzymes involved in cholesterol and fatty acid biosynthesis. It is well documented that AMPK can inactivate 3-hydroxy-3-methylglutaryl-CoA (HMG-CoA) reductase (a key regulatory enzyme in the synthesis of cholesterol and other isoprenoid compounds), acetyl CoA carboxylase (ACC) (the rate limiting enzyme in malonyl CoA synthesis), and hormone-sensitive lipase as well. Concurrently, AMPK triggers fatty acid catabolic pathways to promote ATP production. For instance, AMPK phosphorylates and activates malonyl-CoA decarboxylase (MCD), an enzyme involved in malonyl CoA degradation. More recently, a role for AMPK in inactivating glycerol-3-phosphate acyltransferases has also been suggested in mammalian cells. AMPK, therefore, has the potential to regulate the synthesis and breakdown of triglycerides and cholesteryl esters.

Bioinformatic study of the completed sequence of *Arabidopsis thaliana* and rice genome revealed that, in plants, there are a large group of kinases related to the classical Snf1-type kinases from yeast. In *Arabidopsis*, Snf1-related kinases (SnRKs) are found on all five chromosomes and consist of 38 members. According to sequence similarity, these kinases can be classified into three subgroups: SnRK1 (three members), SnRK2 (ten members) and SnRK3 (25 members) (E. M. Hrabak et al., *Plant Physiol.* 2003, 132, 666-680). The structure of individual kinase is comprised of kinase domain and regulatory domain. Although these kinases show relatively high similarity in the kinase catalytic domain at the N-terminus, their regulatory domains at the C-terminus are highly divergent, which are thought to function in protein-protein interactions or regulate kinase activity (E. M. Hrabak et al., *Plant Physiol.* 2003, 132, 666-680). This underlines complicated functionality for each kinase.

The SnRK1 kinases, based on sequence similarity, are the closest homologues of the yeast Snf1 kinase and the mammalian AMPK. They have been isolated from a variety of species including rye, *Arabidopsis*, tobacco, barley, rice, sugar-beet and potato. The findings that rye and tobacco genes can complement the Snf1 mutation in yeast predict a functional similarity of plant SnRK1 genes to Snf1. Accordingly, the role for plant SnRK1 in sugar metabolism has been suggested. Antisense expression of a SnRK1 in potato resulted in the loss of sugar-inducible expression of sucrose synthase (Purcell et al., *Plant Journal* 1998, 14:195-202). Additional work with these anti-sense lines indicates a potential role for SnRK1 kinases for impacting carbon flow through modulating post-translation modification of ADPglucose pyrophosphorylase, a key regulatory step in starch biosynthesis (Tiessen et al., *Plant Journal* 2003, 35:490-500). Additional supporting evidence came from the finding that anti-sense expression of SnRK1 in barley resulted in little or no starch accumulation in pollen grains, causing male sterility (Y. Zheng et al., *Plant Journal* 2001, 28:431-441).

Unlike SnRK1 group, no representatives of the SnRK2 and SnRK3 groups are found in animals and fungi, predicting their unique regulation of cellular responses in plants. Recently, it has been shown that SnRK3 kinases, also termed as CIPKs (CBL-interacting protein kinases), can interact with a novel family of plant calcium sensors, called calcineurin B-like proteins (CBLs) (Kudla et al., 1999; Shi et al., 1999; Kim et al., 2000). In *Arabidopsis*, ten members exist in the CBL family, each containing three EF-hands binding to calcium (Kolukisaoglu et al., 2004). Under stress conditions, calcium signatures change and decode specific interaction between different CBL and SnRK3 (CIPK) members, leading to altered expression of the downstream genes followed by specific physiological responses. For instance, CBL1 interacts with CIPK7 and CIPK9 to promote drought response, whereas CBL9 activates CIPK3 to enhance cold response. It is noted that the CBL-SnRK3 (CIPK) network largely interacts with the plant hormone abscisic acid (ABA), which is referred to as the stress hormone because of its pivotal roles in stress responses. The evidence supporting this mechanism includes: (i) as in stress conditions, ABA can induce the expression of CBL1 and CIPK3 genes; (ii) cbl9 and cipk3 mutants are hypersensitive to ABA; and (iii) overexpression of a member of SnRK3 group (designated PKS 18, corresponding to annotated At5g45820) in *Arabidopsis* conferred hypersensitivity to ABA during seed germination, whereas silencing of the gene resulted in ABA-insensitivity (D. Gong et al., *J. Biol. Chem.* 2003, 277:42088-42096).

Because of low sequence similarity in the C-terminal domains of the kinases, SnRK2 group can be further divided into two subgroups, namely SnRK2a and SnRK2b (M. Boudsocq et al., *J. Biol. Chem.* 2004, 279:41758-66; T. Umezawa et al., *PNAS* 2004, 101:17306-17311). SnRK2a consist of SnRK2.2, SnRK2.3, SnRK2.6, SnRK2.7 and SnRK2.8. The other five members, SnRK2.1, SnRK2.4, SnRK2.5, SnRK2.9 and SnRK2.10, belong to SnRK2b subgroup (Umezawa et al., *Proc. Natl. Acad. Sci. U.S.A.* 2004, 101:17306-11). Several studies demonstrated that individual kinases in SnRK2 subgroup may have distinct roles in biological processes. For instance, although SnRK2.2 and SnRK2.3 are two protein kinases most closely related to SnRK2.6 based on sequence similarity (Hrabak et al., 2003), they function very differently from SnRK2.6. SnRK2.2 and SnRK2.3 have been shown to be the key protein kinases mediating ABA signaling during seed germination and seedling growth. However, as a positive regulator of ABA signaling, SnRK2.6 is involved in ABA-mediated regulation of stomatal aperture, whereas seed dormancy and germination are not affected in *Arabidopsis* SnRK2.6 mutants (Mustilli et al., 2002; Yoshida et al., 2006).

It is believed that there exist at least three factors underscoring specialized functionality for each kinase in SnRK2 subgroup. First, individual kinases may show different temporal and spatial expression. For instance, SnRK2-8 is expressed abundantly in roots and weakly in leaves and siliques (Umezawa et al., *Proc. Natl. Acad. Sci. U.S.A.* 2004, 101:17306-11); SnRK2-6 is mainly expressed in guard cells and vascular tissues in *Arabidopsis* (Mustilli et al., 2002); and although SnRK2-2 and SnRK2-3 both display the widespread expression in various tissues, SnRK2-3 shows particularly strong expression in root tips (Fujii et al., *Plant Cell*, 2007, 19:485-494). Second, the regulatory domains at the C-terminus are highly divergent among different SnRK2 kinases although the kinase domains are fairly conserved. For instance, overall sequence similarity between SnRK2-4 and SnRK2-6 kinases is 70%, whereas there is only 30% identity in the C-terminal domain. This suggests that the interaction of SNRK2-6 with other signaling components may be different from that of SnRK2-4, thereby predicting different functions conferred by these two kinases. Supporting evidence came from the finding that these two kinases respond to different environmental cues (M. Boudsocq et al., *J. Biol. Chem.* 2004, 279, 41758-66). In addition, the role of the C-terminal domain in controlling the physiological function of the kinases was experimentally verified (Belin et al., 2006; Yoshida et al., 2006). Lastly, slight structure difference of the kinases may lead to different subcellular localization. To understand how each kinase functions, it is necessary to understand where it is localized in a living cell.

BRIEF SUMMARY OF THE INVENTION

One embodiment of the invention is drawn to a process for producing a plant, plant seed or progeny thereof, the process comprising: transforming a plant cell with a nucleic acid sequence encoding a Snf1-related protein kinase protein; growing a plant from the plant cell until the plant produces seed; and harvesting the seed from the plant. Another embodiment of the invention includes a seed harvested from the plant produced by the process of producing the plant. Also included is a plant, plant seed, or progeny thereof having the nucleic acid sequence encoding the Snf1-related protein kinase protein incorporated in a genome thereof.

Another aspect of the invention includes a method of changing the oil, sugar, or starch content of a plant, plant storage organ or plant seed, which process includes introducing a sense or anti-sense nucleic acid construct into a plant transformation vector to produce a modified plant transformation vector, wherein said sense or anti-sense nucleic acid construct comprises the isolated, purified or recombinant nucleic acid sequence encoding an *Arabidopsis* Snf1-related protein kinase (SnRK) protein. The plant, plant storage organ or plant seed's genome is transformed with the modified plant transformation vector. The plant, plant storage organ, or plant seed is grown and oil or biopolymer is then extracted. Genetically transformed plants and plant seeds having a genome that has been transformed by the vector are also included as an additional aspect of the invention. Such plants and plant seeds may be characterized as exhibiting an altered respiration rate, altered seed oil content, altered fatty acid composition, enhanced biomass, enhanced capacity to accumulate biopolymers, and increased root growth compared to a genomically unmodified plant of the same genotype.

In a particular embodiment, a method of modulating the level of Snf1-related protein kinase protein in a plant, includes: stably transforming a plant cell with a plant Snf1-related protein kinase polynucleotide operably linked to a promoter, wherein the polynucleotide is in sense or antisense orientation; and growing the plant cell under plant growing conditions to produce a regenerated plant capable of expressing the polynucleotide for a time sufficient to modulate the Snf1-related protein kinase protein in the plant.

Another embodiment is drawn to a process for extracting oil from a transgenic seed, the process comprising: transforming a plant cell with means for encoding a Snf1-related protein kinase protein; growing a plant from the plant cell until the plant produces seed; harvesting the seed from the plant; and extracting oil from the harvested seed. Oil produced by the process of this process is also included.

Yet another embodiment is drawn to a vector for transformation of plant cells, characterized in that said vector contains a deoxyribonucleic acid sequence according to SEQ ID NO:1 or SEQ ID NO:3, or a part of SEQ ID NO:1 or SEQ ID NO:3, or a sequence that is substantially homologous to SEQ ID NO:1 or SEQ ID NO:3. Also included as an embodiment is a plant or plant seed having a genome, characterized in that said genome contains an introduced nucleotide sequence of SEQ ID NO:1 or SEQ ID NO:3, or a part of SEQ ID NO:1 or SEQ ID NO:3, or a sequence that is substantially homologous to SEQ ID NO:1 or SEQ ID NO:3. Likewise included in particular embodiments are methods of producing transgenic plants by introducing a nucleotide sequence into a genome of said plant, characterized in that said nucleotide sequence introduced into said genome includes SEQ ID NO:1 or SEQ ID NO:3, or a part of SEQ ID NO:1 or SEQ ID NO:3, or a sequence that is substantially homologous to SEQ ID NO:1, or to SEQ ID NO:3, or a part of SEQ ID NO:1 or SEQ ID NO:3.

Another aspect of the invention includes a method of changing the oil content, fatty acid composition, or seed yield of a plant by introducing a sense or anti-sense nucleic acid construct into a plant transformation vector, using the vector to transform the genome of a plant or plant seed, and then growing the plant or plant seed and extracting the oil from the plant seed, characterized in that said nucleic sequence is SEQ ID NO:1 or SEQ ID NO:3, or a part of SEQ ID NO:1 or SEQ ID NO:3, or a sequence that is substantially homologous to SEQ ID NO:1 or SEQ ID NO:3. Yet another aspect of the invention includes a plant, a plant seed, and progeny of a plant that is further transformed by a vector comprising a Snf1-related protein kinase means for altering the oil content of the plant material functionally associated with a promoter.

In yet another embodiment of the invention, a method of altering the drought tolerance of a plant, said method includes: introducing a nucleic acid construct comprising a nucleic acid sequence, selected from the group consisting of SEQ ID NO:1 and SEQ ID NO:3, encoding a polypeptide having Snf-1 related protein kinase activity into a plant transformation vector; transforming the genome of a plant or plant seed with said plant transformation vector; expressing the nucleic acid sequence; growing the plant or plant seed; and selecting a transformed plant having the altered drought tolerance as compared to an average drought tolerance of a statistically significant number of plants of the same genotype as the plant grown in identical conditions, but without the introduced nucleotide sequence.

DETAILED DESCRIPTION OF THE INVENTION

Figure 1:
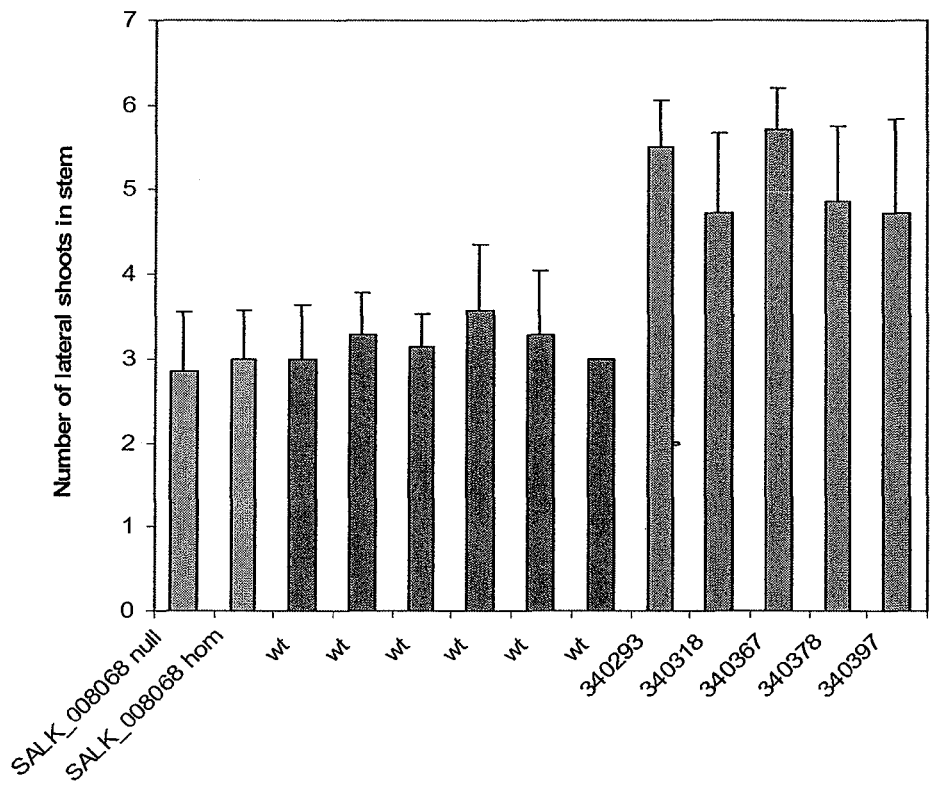
FIG. 1 is a graph showing the comparison of the number of lateral shoots in the stems in 34-day-old wild-type (wt) and SnRK2-6 transgenic lines of *Arabidopsis thaliana* designated as 340293, 340318, 340367, 340378 and 340397. Error bars are ±SD.
Figure 2:
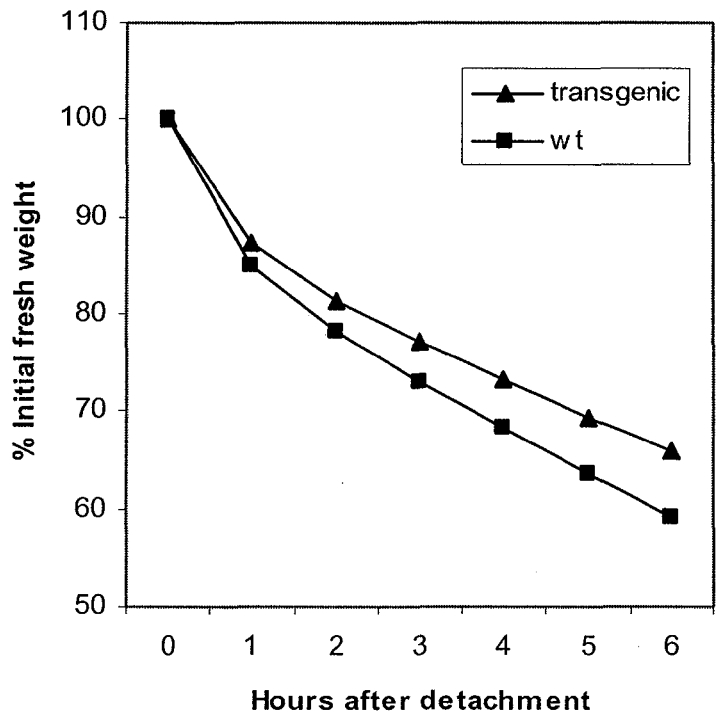
FIG. 2 is a plot showing water loss in detached aerial portions of 27-day-old wild-type (wt) and transgenic lines of *Arabidopsis thaliana*. Each of the data points represents the average of 5 independent transgenic lines of *Arabidopsis thaliana*. The water loss is reported as a percent of initial fresh weight from 0 hours to 6 hours after detachment of the aerial portions from the plant. The significant difference in water loss between wt and transgenic is illustrated by P (ttest) <0.004.

One embodiment of the invention is drawn to identification, isolation and cloning of a genetic element that may be used to modify the natural formation of triacylglycerols in plants in order to increase the yield of commercial plant oils, or to modify their composition to achieve specific commercial improvements of plants and plant products.

Another embodiment of the invention relates to isolation and characterization of Snf1-related protein kinase (SnRK) gene and cDNA sequences from *Arabidopsis* species and to utilization of these sequences in the genetic manipulation of plants.

Yet another embodiment of the invention is to provide a vector containing the full-length SnRK coding sequence or a significant portion of SnRK sequences from *Arabidopsis* in a sense orientation under the control of a promoter (e.g., CsVMV or Ubi1), for re-introducing into *Arabidopsis* species or for introducing into other plants. In an alternative embodiment of the invention, there is provided a vector containing a genomic fragment from *Arabidopsis* consisting of the full-length SnRK gene, or a significant portion of SnRK sequences from *Arabidopsis* species, under the control of its own 5' upstream regulatory sequences, for re-introducing into *Arabidopsis* species or for introducing into other plants.

Also included is a method to construct a vector containing the full-length SnRK sequence or a significant portion of the SnRK sequence from *Arabidopsis*, in an antisense orientation under control of a promoter, for re-introducing into *Arabidopsis* or for introducing into other plants. Another particular method includes modifying *Arabidopsis* and other plants to change their seed oil content, their fatty acid composition, their average seed weight or size, and/or their water loss and plant drought tolerance. Other methods of the invention involve modifying *Arabidopsis* and other plants to promote growth and development, such as increasing root biomass, or to change their photosynthetic activity, thus increasing sugar and starch content.

According to another aspect of the present invention, there is provided a vector containing isolated and purified deoxyribonucleic acid (cDNA) of SEQ ID NO:1 (pSnRKcDNA), for introduction of the cDNA in a sense orientation into a plant cell. As another aspect of the present invention, there is provided a vector containing isolated and purified plant optimized deoxyribonucleic acid (DNA) of SEQ ID NO:3 (pSnRK2-6 hv5 gene), for introduction of the gene in a sense orientation into a plant cell. According to yet another aspect of the invention, there is provided a method for preparing a vector containing SEQ ID NO:1 or a part thereof, or SEQ ID NO:3, or a part thereof, for introduction of the gene or partial gene in an antisense orientation, into a plant cell.

Another embodiment includes providing a mutant seed line of *Arabidopsis thaliana*. The mutant seed line has an insertion mutation in a SnRK gene (as shown in Table 1 below), and produces plants exhibiting increased SnRK activity, resulting in an increase in leaf size and lateral shoot number, decreased water loss, increased sugar and starch content, altered seed fatty acyl composition, increased seed yield, and increased root biomass. The cDNA sequence of the SnRK2-6 is shown in SEQ ID NO:1, the plant-optimized DNA sequence is shown in SEQ ID NO:3 and the translated protein sequence of the SnRK2-6 is shown in SEQ ID NO:2.

The invention also relates to transgenic plants and plant seeds having a genome containing an introduced DNA sequence of SEQ ID NO:1 or SEQ ID NO:3, and a method of producing such plants and plant seeds.

The invention further relates to substantially homologous DNA sequences from plants with deduced amino acid sequences of 25% or greater identity, and 50% or greater similarity, isolated and/or characterized by known methods using the sequence information of SEQ ID NO:1, or SEQ ID NO:3, as will be appreciated by persons skilled in the art, and to parts of reduced length that are still able to function as inhibitors of gene expression by use in an anti-sense or co-suppression (Jorgensen and Napoli 1994) application. It will be appreciated by persons skilled in the art that small changes in the identities of nucleotides in a specific gene sequence may result in reduced or enhanced effectiveness of the genes and that, in some applications (e.g., anti-sense or co-suppression), partial sequences often work as effectively as full length versions. The ways in which the gene sequence can be varied or shortened are well known to persons skilled in the art, as are ways of testing the effectiveness of the altered genes. All such variations of the genes are therefore claimed as part of the present invention.

When considering altered leaf size, lateral shoot number, water loss, or sugar, starch or oil contents or compositions, results from averages of statistically significant numbers of plants or seeds according to the invention are best compared with results from averages of statistically significant numbers of untransformed (control) plants or seeds of the same genotype grown under identical conditions at the same time. This allows for the variability of individual plants of the same genotype, particularly when such plants are grown under different conditions. The actual number of plants or seeds used to form the required average may vary, but should be enough to provide a generally constant average whenever such number is selected. Generally, the number should be at least ten, and is more preferably at least 20, 30, 50 or 100.

The SnRK of the current invention is useful in manipulating SnRK activity, and water loss, drought tolerance, carbon assimilation, plant growth and development, fatty acid bioassembly, and root growth in plants. For example, by transforming plants with a construct containing the SnRK gene in a sense orientation, under the control of a promoter (e.g., CsVMV or Ubi1), the expression of SnRK cDNA and drought tolerance may be enhanced or the composition of the plant altered. This may have particular advantages for altering the drought tolerance and starch/oil ratio in root crops. In some embodiments, plants transformed with a construct containing the SnRk gene may also include additional heterologous or altered genes that further enhance resistance to water loss, drought tolerance, carbon assimilation, plant growth and development, fatty acid bioassembly, and root growth in these plants.

Alternatively, SnRK expression can be silenced to some degree by anti-sense or co-suppression (Transwitch) phenomena (De Lange et al., 1995; Mol et al., 1990; Jorgensen and Napoli, 1994; Kinney, 1995; Vaucheret et al., 1998; Taylor, 1998). For example, silencing SnRK in a seed-specific manner may result in a reduction in SnRK accumulation. This could have applications in reducing the starch, sugar, and/or oil content or ratio in seed root crops to enhance stability during storage.

Some of the manipulations and deliverables which are possible using the SnRK gene or a part thereof, include, but are not limited to, the following: seeds with increased or decreased oil content; leaves containing increased or decreased sugar or starch content; seed oils with an altered fatty acid composition; plants exhibiting decreased water loss; plants exhibiting an enhanced or altered capacity to accumulate storage compounds in other storage organs (e.g., tubers, roots, and leaves); and plants having an increased root growth and biomass.

Several SnRK2 and SnRK3 kinases have been shown to play critical roles in the response to abiotic stress through ABA signaling cascade. This suggests a possibility that some SnRK kinases may function as a regulator of plant lipid metabolism given the vital role of ABA in this metabolism. During seed germination, ABA decreases transcription of the genes involved in fatty acid beta-oxidation and glyoxylate cycle, which are essential pathways for the conversion of the storage lipid, triacylglycerol, into sucrose (S. L. Pritchard et al., *Plant J.* 2002, 31:639-647). On the other hand, ABA increases and behaves as a positive regulator for triacylglycerol synthesis during embryo development. It has been shown that reduction of ABA by seed-specific immunomodulation results in less production of tobacco seed oil (J. Phillips et al., *EMBO J.* 1997, 16:4489-4496). Conversely, treatment of immature maize embryos with ABA (4 μM) elevated the activities of fatty acyltransferases and thus increased oil yield (F. Pacheco-Moises et al., *Plant Physiol.* 1997, 114:1095-1101). This effect has been observed from many other species including *Arabidopsis, Brassica* (napus, juncea and rape), peanut, carrot, wheat, spruce, almond and ground-nut (*Arachis hypogaea*). Nevertheless, it has remained unknown if any SnRK kinases mediate ABA regulation of seed oil synthesis.

In an attempt to identify those key kinases involved in seed oil production, a reverse genetic approach was used. This is based on screening of SALK T-DNA insertion into the genes, followed by determining the impact of the gene knockout on seed oil content and seed yield. After large scale screening, the role of SnRK2-6 gene (At4g33950) in seed oil production was uncovered. This gene, also named OST1 (OPEN STOMATA 1), was previously demonstrated to encode the protein possessing calcium-dependent protein serine/threonine kinase activity and regulate ABA-mediated stomatal aperture (Mustilli et al., 2002). Inactivation of this gene by T-DNA insertion resulted in 24% to 50% reduction in seed yield under dehydration condition. In addition, a 7% to 25% decrease in seed oil content was detected in the knockout line SALK-008068. However, protein content only showed little change between plants homozygous for the insertion (21.3%) and null segregants (20.9%), indicating that SnRK2-6, a member of SnRK2a subgroup, acts as a positive regulator for seed oil production.

SnRK2-6 was previously identified as a regulator of ABA-mediated stomatal conductance, which is preferentially expressed in stomata and vascular tissues in *Arabidopsis* (Mustilli et al., 2002; Fujii et al., *Plant Cell* 2007, 19:485-494). Reverse genetic studies in the present invention uncovered its role in seed oil production.

SnRK2-6 was ectopically expressed under a constitutive promoter, CsVMV, in *Arabidopsis*. The forced ectopic expression of SnRK2-6 by CsVMV may disrupt highly spatially localized pattern of SnRK2-6 expression driven by the native promoter, giving rise to a pattern different from normal. Such perturbation may influence plant growth and metabolisms.

Figure 3:
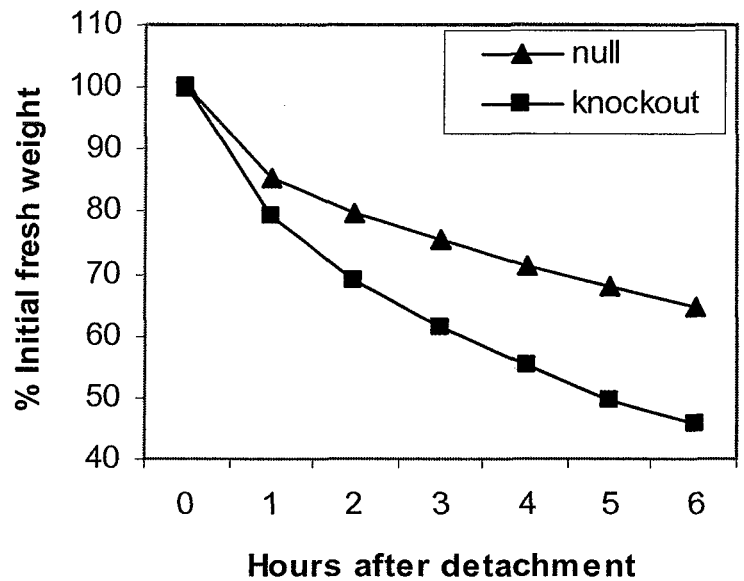
FIG. 3 is a plot showing water loss in detached aerial portions of 27-day-old homozygous (knockout) and null (null) for T-DNA insertion in SALK_008068 in *Arabidopsis thaliana*. The water loss is reported as a percent of initial fresh weight from 0 hours to 6 hours after detachment of the aerial portions from the plant. The significant difference in water loss between wt and transgenic is illustrated by P (ttest) <0.004.

Referring to FIG. 1, overexpression of SnRK2-6 in *Arabidopsis* was demonstrated to promote leaf growth, and further to increase lateral shoot number. Additionally, water loss was shown to be substantially reduced in the excised transgenic plants compared to wild-type plants demonstrating that overexpression of SnRK2-6 may reduce transpiration rate of aerial parts of the plants. In contrast, knockout of this gene accelerated water loss, as shown in FIG. 3.

Figure 4:
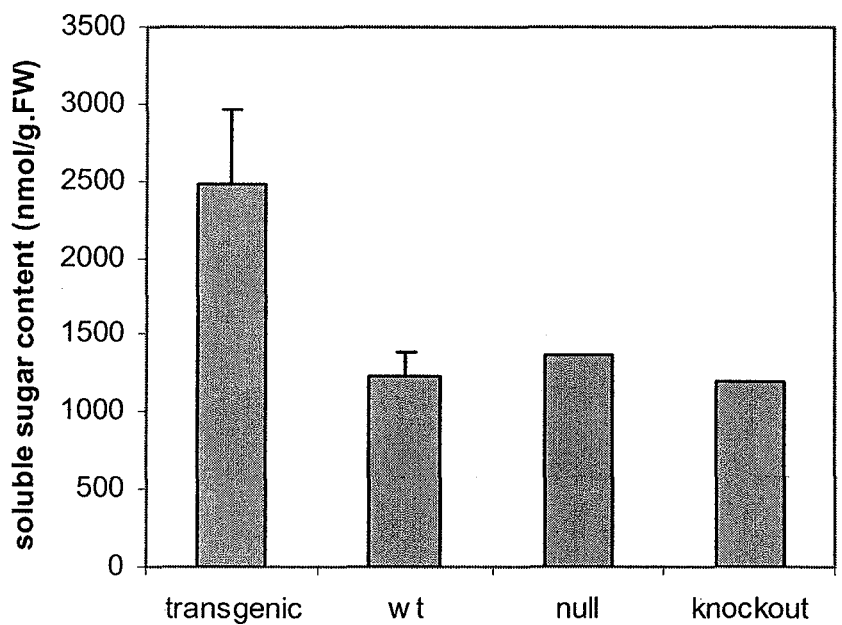
FIG. 4 is a graph showing soluble sugar content (nmol/g of glucose, fructose and sucrose) in leaves from 30-day-old wild-type (wt) and T3 SnRK2-6 transgenic lines (340293, 340318, 340367, 340378 and 340397) of *Arabidopsis thaliana*. Each of the data points represents the average of five independent SnRK2-6 transgenic lines of *Arabidopsis thaliana* (340293, 340318, 340367, 340378 and 340397). Error bars are ±SD (n=8 or 10 plants of each line sampled).
Figure 5:
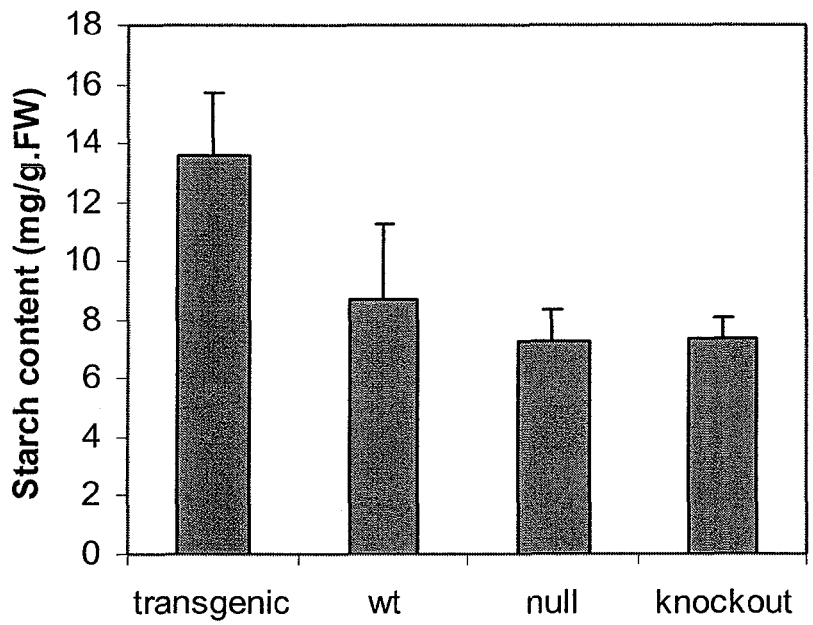
FIG. 5 is a graph showing starch content in leaves from 30-day-old wild-type (wt) and five independent SnRK2-6 transgenic lines of *Arabidopsis thaliana*. Each of the data points represents the average of five independent SnRK2-6 transgenic lines of *Arabidopsis thaliana* (340293, 340318, 340367, 340378 and 340397). The starch content is reported as nmol/g of the total starch content of leaves from each line. Error bars are ±SD (n=8 or 10 plants of each line sampled).

As shown in FIG. 4, increased carbon assimilation in transgenic *Arabidopsis* plants may demonstrate that overexpression of SnRK2-6 may promote plant growth. More specifically, transgenic *Arabidopsis* plants overexpressing SnRK2-6 showed a dramatic increase in the contents of fructose, glucose and sucrose in the transgenic leaves under normal greenhouse conditions. Total sugar content in the transgenic leaves was twice as much as in the wild-type leaves. Starch content of the transgenic plants was actually 156% of wild type level. Referring to FIGS. 4 and 5, the knockout of SnRK2-6 did not largely affect either soluble sugar or starch content. Collectively, these results indicate that the constitutive expression of the SnRK2-6 transgene can increase leaf photosynthetic activity leading to increased carbon assimilation.

Figure 6:
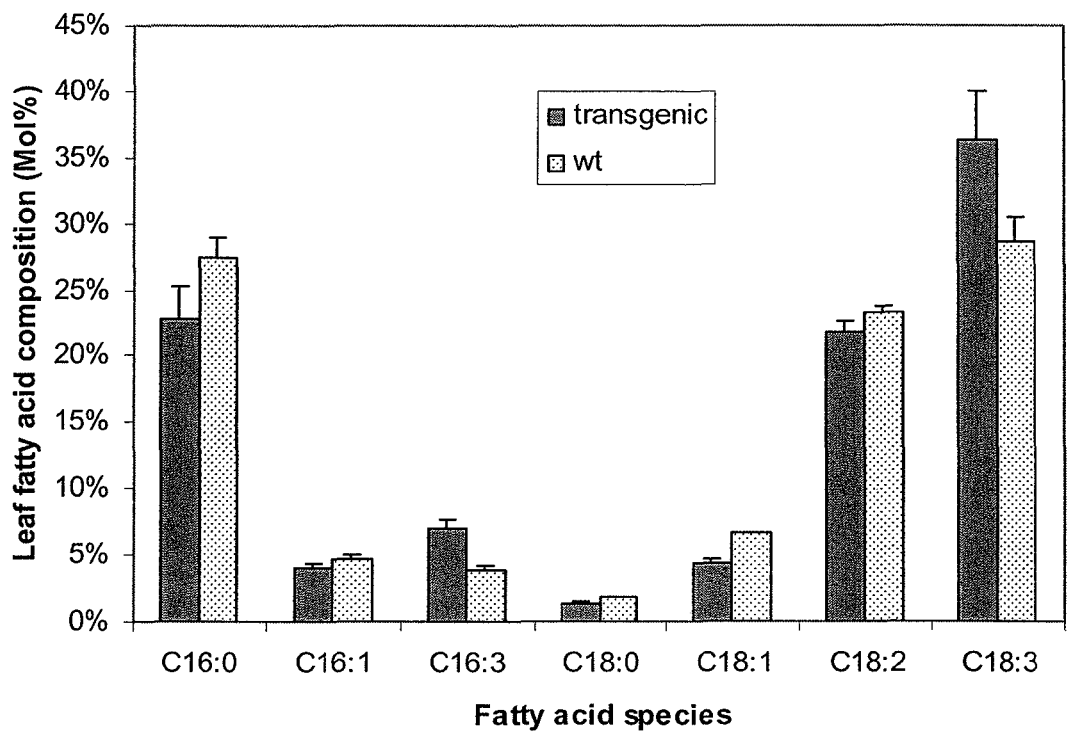
FIG. 6 is a graph showing a comparison of the fatty acid composition of leaves from wild-type (wt) and SnRK2-6 transgenic lines of *Arabidopsis thaliana*. Each of the data points represents the average of five independent SnRK2-6 transgenic lines of *Arabidopsis thaliana* (340293, 340318, 340367, 340378 and 340397). Proportions of fatty acids are reported as Mol % of the total composition of leaves from each line. Error bars are ±SD (n=10 plants of each line sampled).

FIG. 6 shows the dramatic change in fatty acid composition in the transgenic leaves. Two trienoic fatty acids, 16:3 and 18:3, in leaves of the transgenic plants increased by 81% and 26%, respectively, relative to wild type, indicating the desaturation processes is strengthened by the transgene.

Figure 7:
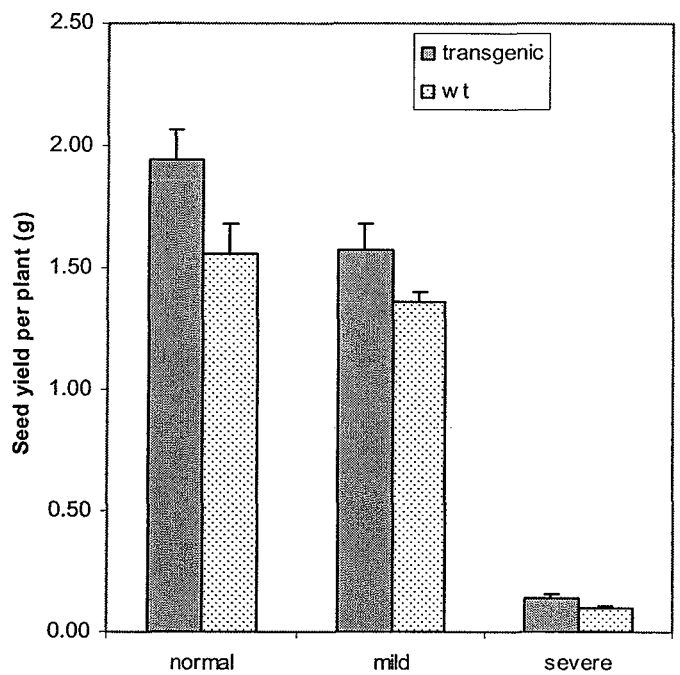
FIG. 7 is a graph showing a comparison of the seed yield per plant in wild-type (wt) and SnRK2-6 transgenic lines of *Arabidopsis thaliana*. More specifically, it is a comparison of the seed yield under normal, mild and severe growth conditions. Plants grown under "normal" conditions were watered well during the entire growth cycle. Irrigation was ceased for 6 days during the flowering stage in plants grown under "mild" conditions. Irrigation was ceased for 16 days during the vegetative stage in plants grown under "severe" conditions. Error bars are ±SD (n=30 plants of each line sampled). The significant difference in seed yield between wt and transgenic lines is illustrated by P (ttest)<0.001.

Consistent with increased photosynthetic activity in the leaves, a drastic increase in seed yield in transgenic plants was detected. As compared to wild type plants, the transgenic plants showed a 24%, 16% and 35% increase in seed yield, respectively, under normal conditions, mild drought conditions, and severe drought conditions (FIG. 7). The results suggest that the transgene not only enhances plant drought tolerance, but also alter other physiological processes, leading to increased seed production under normal growth condition.

Seed oil analysis showed that CsVMV-driven expression of SnRK2-6 did not result in a significant change in seed oil content. However, overall seed oil production increased by the transgene due to increased seed yield.

Taken together, the constitutive overexpression of SnRK2-6 drastically increased the contents of soluble sugars and starch and altered lipid biosynthesis in *Arabidopsis* leaves. This further resulted in a large increase in seed yield under both normal and drought conditions.

Figure 10:
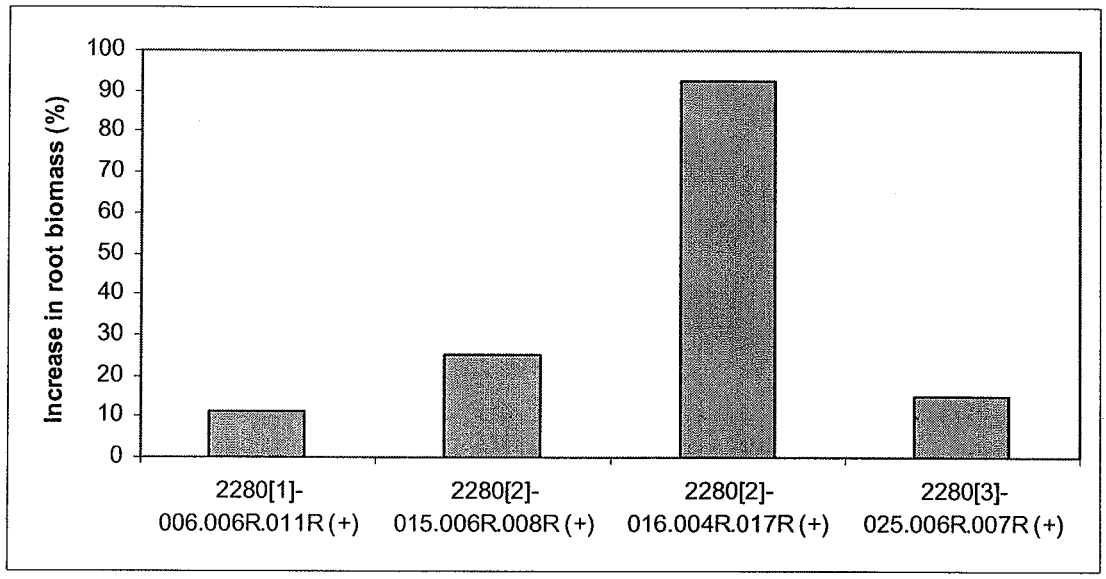
FIG. 10 is a graph showing a comparison of the root biomass in null segregants (null) and SnRK2-6-containing corn plants (transgenic) from four independent lines, which are designated as 2280(1)006.006R.011R, 2280(2)015 .006R.008R, 2280(2)016.004R.017R and 2280(3) 025.006R.007R. Aerial portions were cut and the roots were collected by removing soil and then dried in greenhouse for 7 days to eliminate moisture variation among different samples.

As shown in FIG. 10, increased root biomass in transgenic corn plants may demonstrate that overexpression of SnRK2-6 may promote root growth. The transgenic corn plants overexpressing SnRK2-6 showed a dramatic increase in root biomass (i.e., 11%, 25%, 92%, and 15%) in comparison to null plants. These results indicate that SnRK2-6 kinase can increase root growth. Such a mechanism may be associated with the increase corn drought tolerance.

Particularly preferred plants for modification according to the present invention include *Arabidopsis thaliana*, borage (*Borago* spp.), Canola, castor (*Ricinus communis*), cocoa bean (*Theobroma cacao*), corn (*Zea mays*), cotton (*Gossypium* spp), Crambe spp., Cuphea spp., flax (*Linum* spp.), Lesquerella and Limnanthes spp., Linola, nasturtium (*Tropaeolum* spp.), *Oenothera* spp., olive (*Olea* spp.), palm (*Elaeis* spp.), peanut (*Arachis* spp.), rapeseed, safflower (*Carthamus* spp.), soybean (*Glycine* and *Soja* spp.), sunflower (*Helianthus* spp.), tobacco (*Nicotiana* spp.), *Vernonia* spp., wheat (*Triticum* spp.), barley (*Hordeum* spp.), rice (*Oryza* spp.), oat (*Avena* spp.) sorghum (*Sorghum* spp.), rye (*Secale* spp.) or other members of the Gramineae.

The present invention is particularly useful when used to modify the yield or composition of oilseed produced from oilseed crops. Oilseed crops are plant species that are capable of generating edible or industrially useful oils in commercially significant yields, and include many of the plant species listed above. Such oilseed crops are well known to persons skilled in the art.

The SnRK2-6 gene may be introduced with one or more other genes that confer desirable traits in plants. For example, a stress tolerance gene or a drought tolerance gene may, optionally, be introduced in combination with the SnRK2-6 gene.

The invention is further described by use of the following illustrative examples.

EXAMPLES

Example 1

Identification of T-DNA Insertion into *Arabidopsis* SnRK Genes by PCR

According to sequence similarity, *Arabidopsis* SnRK kinases can be divided into three subgroups, SnRK1, SnRK2 and SnRK3. SnRK1 subgroup includes three kinases encoded by At3g01090, At3g29160, and At5g39440, respectively. SnRK2 subgroup consists of ten members corresponding to the genes At4g40010, At2g23030, At1g60940, At1g10940, At5g63650, At5g08590, At1g78290, At3g50500, At5g66880, and At4g33950, respectively. SnRK3 is the largest subgroup with 25 members encoded by the genes: At5g57630, At3g17510, At1g48260, At4g24400, At5g35410, At2g26980, At1g30270, At1g01140, At4g14580, At3g23000, At2g38490, At5g01820, At2g30360, At2g34180, At1g29230, At5g45810, At4g18700, At4g30960, At5g45820, At5g58380, At5g07070, At5g01810, At2g25090, At5g25110, and At5g10930.

In SALK lines with T-DNA insertion into SnRK genes, plants homozygous, heterozygous and null for the insertion were screened by PCR as shown in Tables 1 and 2. Genomic DNA used in PCR reactions was isolated from *Arabidopsis* leaves. As an example, GSP108 and LBa1 primers were used to screen for plants carrying the T-DNA insertion into SnRK2-6 (At4g33950) in SALK 008068. On the other hand, GSP108 and GSP124, two gene-specific primers of At4g33950, were used to determine if a wild-type copy of the gene is present in the segregants of SALK 008068.

TABLE 1

The SnRK gene family and the corresponding SALK T-DNA insertion lines

| Gene name | SALK lines | Insertion position | Gene-specific primer |
|---|---|---|---|
| SnRK1 group (3) | | | |
| At3g01090 (Akin10) | | | |
| At3g29160 (Akin11) | | | |
| At5g39440 | | | |
| SnRK2 group (10) | | | |
| At4g40010 (SnRK2-7) | SALK_042333 (S1) | intron | GSP101 |
| At2g23030 (SnRK2-9) | SALK_152137 (S25) | exon | GSP127 and GSP126* |
| At1g60940 (SnRK2-10) | SALK_064987 (S3) | 300-UTR3 | |
| At1g10940 (SnRK2-4) | SALK_080588 (S4) | exon | GSP103 |
| At5g63650 (SnRK2-5) | SALK_075624 (S5) | exon | GSP104 |
| At5g08590 (SnRK2-1) | | | |
| At1g78290 (SnRK2-8) | SALK_031421 (S7) | intron | GSP106 |
| | SALK_069354 (S8) | exon | GSP106 |
| At3g50500 (SnRK2-2) | | | |
| At5g66880 (SnRK2-3) | SALK_096546 (S9) | exon | GSP107 |
| At4g33950 (SnRK2-6) | SALK_008068 (S10) | intron | GSP108 and GSP124* |
| SnRK3 group (25) | | | |
| At5g57630 (CIPK21) | | | |
| At3g17510 (CIPK1) | | | |
| At1g48260 (CIPK17) | SALK_062790 (S27) | exon | GSP131 and GSP130* |
| At4g24400 (CIPK8) | | | |
| At5g35410 (CIPK24, SOS2) | SALK_016683 (S11) | intron | GSP109 |
| At2g26980 (CIPK3) | SALK_033968 (S12) | exon | |
| | SALK_064491 (S12-1) | | GSP122, GSP123 and GSP121* |
| At1g30270 (CIPK23) | SALK_032341 (S13) | intron | GSP110 |
| At1g01140 (CIPK9) | SALK_014699 (S14) | intron | GSP111 |
| At4g14580 (CIPK4) | SALK_009893 (S15) | exon | GSP112 |
| At3g23000 (CIPK7) | SALK_055008 (S16) | exon | GSP113 |
| At2g38490 (CIPK22) | SALK_135490 (S28) | exon | GSP133 and GSP132* |
| At5g01820 (CIPK14) | SALK_009699 (S17) | exon | GSP114 |
| At2g30360 (CIPK11) | SALK_055565 (S18) | exon | GSP115 and GSP125* |
| At2g34180 (CIPK13) | SALK_124748 (S19) | exon | GSP116 |
| At1g29230 (CIPK18) | SALK_011025 (S20) | 300-UTR5 | GSP117 |
| At5g45810 (CIPK19) | SALK_044735 (S21) | exon | GSP118 |
| At4g18700 (CIPK12) | SALK_039840 (S22) | 1000-P | |
| At4g30960 (CIPK6) | | | |
| At5g45820 (CIPK20) | SALK_040637 (S23) | 1000-P | GSP119 |
| At5g58380 (CIPK10) | SALK_111320 (S24) | exon | GSP120 |
| At5g07070 (CIPK2) | | | |
| At5g01810 (CIPK15) | | | |
| At2g25090 (CIPK16) | | | |
| At5g25110 (CIPK25) | SALK_079011 (S29) | exon | GSP135 and GSP134* |
| At5g10930 (CIPK5) | SALK_084456 (S26) | exon | GSP128 and GSP129* |

*stands for GSP (gene-specific primer) which has the same direction as LBa1;
"S#" is DAS internal sample number.

TABLE 2

The nucleotide sequences of gene-specific primers and LBa1

| Primer name | Nucleotide sequence | |
|---|---|---|
| LBa1 | 5'-TGGTTCACGTAGTGGGCCATCG-3' | (SEQ ID NO: 7) |
| GSP101 | 5'-TCTTGGTTCCGGTAACTTTGGA-3' | (SEQ ID NO: 8) |
| GSP103 | 5'-CCAACGACGACTTCTTTCTT-3' | (SEQ ID NO: 9) |
| GSP104 | 5'-TTGGTCAATTGCGTAGATAAAG-3' | (SEQ ID NO: 10) |
| GSP106 | 5'-GCAAAGCAGCTTCCCAAGAAGA-3' | (SEQ ID NO: 11) |
| GSP107 | 5'-CTCCGCTACTGTCAATGTCGAT-3' | (SEQ ID NO: 12) |
| GSP108 | 5'-GCAGTGAGTGGTCCAATGGATT-3' | (SEQ ID NO: 13) |
| GSP109 | 5'-GCTCAAGAAGCAAATCTTCCAATC-3' | (SEQ ID NO: 14) |
| GSP110 | 5'-TCTCGCTTGCTGTTACTCGCTT-3' | (SEQ ID NO: 15) |
| GSP111 | 5'-CCTTAAAACCAGGCAGCCACTA-3' | (SEQ ID NO: 16) |
| GSP112 | 5'-ATCACAGGGACAGTTCTTCTCG-3' | (SEQ ID NO: 17) |
| GSP113 | 5'-TCAGGCACCATTTTCTCCTTCC-3' | (SEQ ID NO: 18) |
| GSP114 | 5'-CCGAATCCTCCCAATTTGTCTG-3' | (SEQ ID NO: 19) |
| GSP115 | 5'-AGAAACCAAATCCAACCAACGA-3' | (SEQ ID NO: 20) |

TABLE 2-continued

The nucleotide sequences of
gene-specific primers and LBa1

| Primer name | Nucleotide sequence | |
|---|---|---|
| GSP116 | 5'-CCCAACGCCAATACAATTCATG-3' | (SEQ ID NO: 21) |
| GSP117 | 5'-TTTCTCCAGCTCTGGTCTGAGTTC-3' | (SEQ ID NO: 22) |
| GSP118 | 5'-GAAGAAGCAGGATCAGAGCAATCA-3' | (SEQ ID NO: 23) |
| GSP119 | 5'-GTTGTTTCCTTGCCATTTCCAA-3' | (SEQ ID NO: 24) |
| GSP120 | 5'-GTAAGCTCATCTTTCTCACCCTGC-3' | (SEQ ID NO: 25) |
| GSP121 | 5'-TCGGAGACAGCAAGTGAAACG-3' | (SEQ ID NO: 26) |
| GSP122 | 5'-TTTTGAACATCGAAACCGAGA-3' | (SEQ ID NO: 27) |
| GSP123 | 5'-GAAGACTTGGCGCTACTTGGAA-3' | (SEQ ID NO: 28) |
| GSP124 | 5'-CCGCTACTGTCGATGTCAAGA-3' | (SEQ ID NO: 29) |
| GSP125 | 5'-ATGCCAGAGATCGAGATTGCC-3' | (SEQ ID NO: 30) |
| GSP126 | 5'-TGGTGAAGGATTTAGGATTTGG-3' | (SEQ ID NO: 31) |
| GSP127 | 5'-TTATCTGATCCAAGCGATTCGA-3' | (SEQ ID NO: 32) |
| GSP129 | 5'-ATGGAGGAAGAACGGCGAGTTC-3' | (SEQ ID NO: 33) |
| GSP130 | 5'-GATGATGAGCCCAGCTCATTCA-3' | (SEQ ID NO: 34) |
| GSP131 | 5'-GGTGATAAAGGGAATGCGTGTT-3' | (SEQ ID NO: 35) |
| GSP132 | 5'-AACCGGTTGGTTAATCAAACGA-3' | (SEQ ID NO: 36) |
| GSP133 | 5'-TGGCCGAAGACTCTAATTCTTC-3' | (SEQ ID NO: 37) |
| GSP134 | 5'-TATGATTATCACCGTGCCACGA-3' | (SEQ ID NO: 38) |

In combination with LBa1 (the T-DNA left border primer), GSPs were used for PCR screening of plants carrying T-DNA insertion into the SnRK genes.

To establish the function for each kinase in seed oil production, oil profiles in the seeds of SALK lines carrying the insertion into the kinase genes were determined by gas chromatography. To better assess the impact caused by the disruption of the kinase genes, null siblings from the same lines were used as control. Theoretically, null siblings have higher similarity in genetic background to other segregants homozygous and heterozygous for the insertion as compared to wild type.

Example 2

*Arabidopsis* Seed Fatty Acid Methyl Ester Analysis

Extraction and Derivatization of *Arabidopsis* Seeds

Mature *Arabidopsis* seeds were harvested and all non-seed plant matter removed. From the total seed harvested, ~10 mg aliquots were taken and distributed into 1 ml capacity 96-well plate. Precise weight measurements were obtained by the use of an analytical balance with and accuracy of +/−2 μg and recorded. The well plate was rinsed with hexane prior to use and two 4 mm diameter stainless steel homogenizing bead placed into each well. After sample distribution, 0.4 ml hexane containing 75 ppm methyl heptadecanoate and 0.2 ml 0.5 M sodium methoxide was dispensed to each well. The well plate was then capped and placed into a vertical shaker for two minutes at 500 strokes per minute then changed to 58 minutes at 250 strokes per minute. Once shaking was complete, the well plate was then centrifuged for five minutes at 5600 rcf. After centrifuging, the top hexane extract layer was taken and placed into another 96-well plate. This extraction was performed twice more with 0.4 ml hexane, combining each subsequent extract with the first. The second and third extraction vertical shaking conditions were changed to 30 minutes at 250 strokes per minute per extraction. The combined 1.2 ml hexane extracts were diluted 10 fold into another 96-well plate for analysis by GC-FID.

Fatty Acid Methyl Ester (FAME) Analysis

The resulting fatty acid methyl esters *Arabidopsis* seed lipids were resolved on a SGE BPX70 capilary column (15 m, ID 0.22, df 0.25) using a three ramp temperature gradient with 1 ml/minute hydrogen as the carrier gas (60° C. held for 1.34 minutes, 41.3° C./minute to 150° C., 9.1° C./minute to 180° C., 41.3° C./minute to 220° C. held for 1.86 minutes). Inlet temperature was 230° C. and flame ionization detector temperature was 240° C. Identification and quantitation of the FAME analysis by retention time was accomplished with a rapeseed oil reference standard (manufactured by Matreya) with 75 ppm methyl heptadecanoate.

Example 3

*Arabidopsis* Leaf Fatty Acid Methyl Ester Analysis

Extraction and Derivatization of *Arabidopsis* Leaf Lipids

Frozen *Arabidopsis* leaves were ground to fine powder under liquid nitrogen by using mortar and pestle. From this powder ~50 mg aliquots were taken and distributed into 1 ml capacity 96-well plate. The well plate was rinsed with hexane prior to use and a 4-mm diameter stainless steel homogenizing bead placed into each well. After sample distribution, 0.5 ml hexane and 0.25 ml 0.5 M sodium methoxide was dispensed to each well. The well plate was then capped and placed into a vertical shaker for 30 minutes at 250 strokes per minute. The well plate was then centrifuged for 5 minutes at 5600 rcf. After centrifuging, the top hexane extract layer was taken and placed into another 96-well plate for analysis by gas chromatograph flame ionization.

FAME's Analysis

The resulting fatty acid methyl esters *Arabidopsis* leaf lipids were resolved on a SGE BPX70 capilary column (15 m, ID 0.22, df 0.25) using a three ramp temperature gradient with 1 ml/minute hydrogen as the carrier gas (60° C. held for 1.34 minutes, 41.3° C./minute to 150° C., 9.1° C./minute to 180° C., 41.3° C./minute to 220° C. held for 1.86 minutes). Inlet temperature was 230° C. and flame ionization detector temperature was 240° C. Identification of FAME's by retention time was accomplished with a rapeseed oil reference standard (manufactured by Matreya).

Example 4

*Arabidopsis* Seed Total Protein Analysis

Acidic Digestion of *Arabidopsis* Seeds (Protein Hydrolysis)

Mature *Arabidopsis* seeds were harvested and all non-seed plant matter removed. From the total seed harvested, ~20 mg aliquots were taken and distributed into 2 ml autoclaveable centrifuge tubes with rubber o-ringed screw caps. Precise weight measurements were obtained by the use of an analytical balance with and accuracy of +/−2 μg and recorded. Ten acid washed 4-mm glass beads were added to each centrifuge tube prior to use. After sample distribution, the centrifuge tubes were placed onto a vertical shaker at 500 strokes per minute for five minutes. Then 1.4 ml of 6 N hydrochloric acid with 0.1% phenol and 1% 2-mercaptoethanol was added to each sample. The centrifuge tubes were then placed back onto a vertical shaker for 15 minutes at 500 strokes per minute. After vertical shaking was complete, the centrifuge tubes were placed onto a heating block at 100° C. for 24 hours completing the digestion. Once the digestion process was finished, the centrifuge tubes were cooled to room temperature and digest filtered through a 0.4 µm glass filter. 0.1 ml of the filtered digested was diluted in a 1.5 ml glass injection vial with 0.3 ml 2 N sodium hydroxide, 0.6 ml water, and 0.1 ml water with 1000 pmol/µl norvaline as an internal standard for analysis by High Performance Liquid Chromatography Fluorescence Detection.

Derivatization of Amino Acid Residues

Primary amino acids were derivatized with o-phthalaldehyde (OPA). Secondary amino acids were derivatized with 9-fluorenylmethyl chloroformate (FMOC). Both derivatization reactions were accomplished pre-column using the HPLC injection loop. Samples were first buffered with 0.4 N borate buffer at 10.2 pH (4 µl buffer to 1 µl sample) and then mixed with OPA and FMOC (1 µl OPA and 1 µl FMOC in order). The samples were then injected for analysis.

Analysis of Amino Acid Residues by HPLC-FLD

Derivatized amino acid residues were resolved on a 150× 3.0 mm 5 µm C18(2) reverse phase column with a 40° C. binary elution gradient. The aqueous phase (eluent A) consisted of 40 mM sodium phosphate buffer at 7.8 pH and the organic phase (eluent B) consisted of acetonitrile:methanol: water (45:45:10 v/v/v). The solvent gradient system was 0-1.9 min A/B (%) 100:0; 1.9-18.1 min A/B (%) 43:57; 18.1-18.6 min A/B (%) 0:100; 18.6-22.3 min A/B (%) 0:100; 22.3-23.2 min A/B (%) 100:0; 23.2-26 A/B (%) 100:0. The flow was a constant 2 ml/minute.

The fluorescent detector parameters were set for excitation at 340 nm and emission at 450 nm for the first 15 minutes of the analysis. The detector then switches to 266 nm excitation and 305 nm emission for the remainder of the analysis time. The first 15 minutes of analysis is optimized for the detection of OPA derivative residues and the remainder for FMOC derivative residues.

Identification and quantitation of amino acid residues was calibrated with amino acid standard mixes (purchased from Agilent Technologies) containing 90.9 pmol/µl norvaline internal standard. Residues quantitated were aspartic acid, glutamic acid, serine, histidine, glycine, threonine, arginine, alanine, tyrosine, valine, methionine, phenylalanine, isoleucine, leucine, lysine, and proline. The recovered mass of each residue was calculated, summed together giving a total approximate protein mass, and then calculated into a percent protein for each *Arabidopsis* seed sample.

Example 5

Total Starch Analysis for Fresh *Arabidopsis*

Fresh *Arabidopsis* leaves were ground to a very fine powder under liquid nitrogen by grinding tissue in a mortar and pestle. The samples were de-sugared by 80% ethanol prior to starch analysis. Digestion of starch was conducted with α-amylase and amyloglucosidase, respectively. The released glucose was detected by glucose oxidase- and peroxidase-based enzyme assay. Starch content was calculated based on the released glucose with adjustment of free glucose to starch.

Example 6

LC/MSMS Metabolite Analysis

*Arabidopsis* leaf tissue was ground manually with liquid nitrogen and a mortar and pestle to obtain a very fine powder sample. Approximately 100 mg of finely ground leaf tissue was extracted with an 80:20 methanol; 0.1N HCl solution and mixed well resulting in a 350 mg/mL extraction. Samples were centrifuged to pellet particulates and an aliquot of the supernatant containing the extracted metabolites was removed, diluted 1:10 with 80:20 acetonitrile:water containing a stable isotope of glucose as an internal standard, and analyzed by liquid chromatography with tandem mass spectrometric detection (LC-MS/MS).

LC-MS/MS provides selectivity and sensitivity suitable for quantitative analysis of primary and secondary metabolites in complex biological matrices such as seed tissue extracts. A liquid chromatographic separation prior to MS/MS quantitation is desirable to separate the compounds of interest from matrix components that may suppress the ionization/response of the compound of interest. Several techniques are available to ionize the analytes including positive (+) or negative (−) electro spray ionization (ESI) and +/−atmospheric chemical ionization (APCI). MS/MS analysis of compounds is essentially a four-step process: 1) formation of a molecular ion specific to the compound of interest; 2) selection of the molecular ions; 3) formation of compound specific fragment ions; 4) detection of the compound specific fragment ions. The eluent from the LC column is introduced into the MS, which continuously performs the four-step process on a millisecond timeframe.

The LC-MSMS analyses in this study was performed on an Agilent 1100 liquid chromatograph interfaced to an Applied Biosystems Sciex™ 3000 triple quadrapole tandem mass spectrometer equipped with a Turbolon™ Spray inlet. Prior to LC-MS/MS analysis of seed tissue extracts, standards (~10 µg/mL) of the individual secondary metabolites were infused (10 µL/minute) into the mass spectrometer in order to establish the following parameters:

Q1—m/z of +/−molecular ion

DP—declustering potential for maximum formation of molecular ion

Q3—m/z of product ions generated from the molecular ion

CE—collision energy for maximum formation of product ions

CXP—cell exit potential

The *Arabidopsis* metabolites monitored in this study were found to form the expected [M−H]⁻ molecular ion using negative mode ESI, Q1, as shown in Table 3 below. The fragment ions used for quantitation for each of the metabolites are listed in the table below, Q3. The following table lists the MSMS parameters used to quantitate each of the metabolites (G1P=glucose-1-phosphate, G6P=glucose-6-phosphate, ADP-g=adenosine diphosphate-glucose, GDP-g=guanosine 5'-diphosphate-glucose, UDP-g=uridine 5'-diphosphate-glucose).

TABLE 3

| | Fragment ions | | | | |
|---|---|---|---|---|---|
| | m/z | | | CE | |
| Analyte | Q1 | Q3 | DP (V) | (V) | CXP (V) |
| G6P | 258.9 | 139.1 | −34 | −21 | −6 |
| G1P | 258.8 | 240.9 | −32 | −18 | −14 |
| ADP-g | 588.1 | 345.9 | −35 | −35 | −22 |
| GDP-g | 604.2 | 361.8 | −33 | −36 | −22 |
| UDP-g | 565.1 | 322.9 | −35 | −34 | −22 |
| Fructose | 179.0 | 113.1 | −29 | −12 | −5 |
| Glucose | 179.0 | 119.1 | −30 | −10 | −5 |
| Sucrose | 341.1 | 178.9 | −56 | −20 | −10 |

Because of the high polarity of the *Arabidopsis* metabolites of interest, a HILIC phase liquid chromatographic column (TSKgel Amide 80, TOSOH Biosciences LLC, 100×2 mm, 5 μM) was used for separation. A linear gradient starting at 0:100 HPLC water:acetonitrile going to 100:0 water:acetonitrile over four minutes at a flow rate of 500 μL/minute was used. To enhance compound ionization, the water was buffered with 10 mM ammonium acetate.

Quantitation was achieved by creating a calibration curve for each targeted metabolite and using linear regression analysis on each extract. The concentration found in the extract multiplied by the dilution factor (10) to obtain a total nmol $g^{-1}$ concentration in the sample. All data presented is the mean of six replicates, three analytical replicates and two greenhouse replicates.

Example 7

Construction of SnRK2-6 Expression Vector for *Arabidopsis* Transformation

Figure 11:
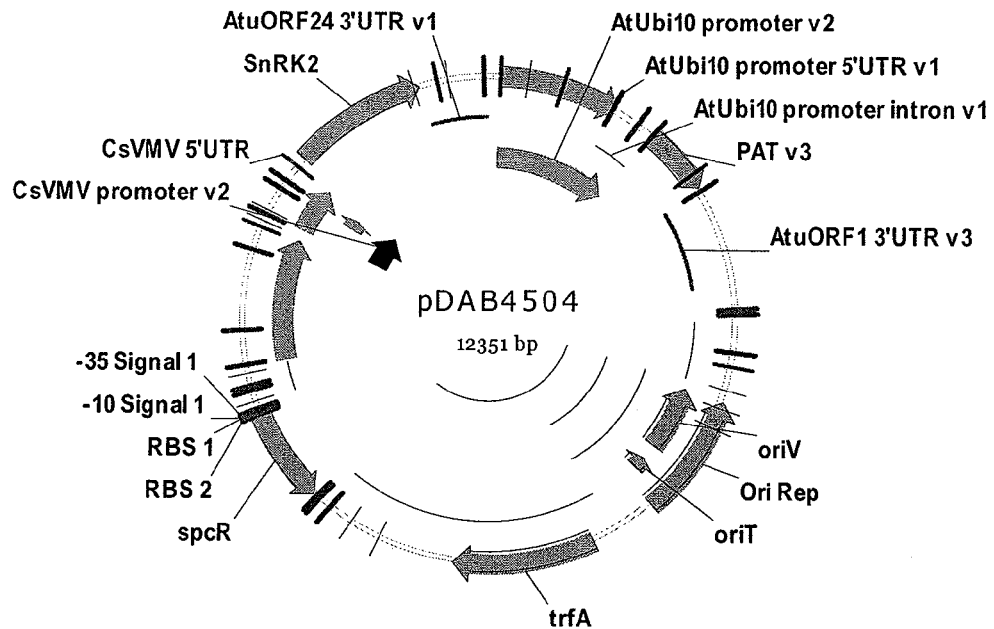
FIG. 11 a map of plasmid pDAB4504 which may be used as a vector. The vector contains the following salient features for plant transformation in the current invention: a CsVMV promoter, SnRK2-6 and an AtuORF24 3'-UTR.

To amplify *Arabidopsis* SnRK2-6 gene, total RNA (900 ng) isolated from *Arabidopsis* leaves was used for single strand cDNA synthesis using Oligo dT20 as primer (Invitrogen SuperScriptIII RT kit). The sscDNA was further amplified using a pair of primers, 5'-TAA TTT CCATGGATC GAC CAG CAG TGA GT-3' and 5'-TTT TTT CCATGGATC ACA TTG CGT ACA CAA TCT CT-3', both of which include a Nco I site (underlined). The amplified SnRK2-6 gene was then digested with Nco I and inserted into the gateway entry vector pDAB3731. The insert orientation was determined by sequencing. The resulting plant transcription unit (PTU) comprising CsVMV, SnRK2-6 and AtuORF24 3'-UTR was cloned into the binary gateway destination vector pDAB3725 using gateway LR reaction. The resulting plasmid, designated pDAB4504 (FIG. 11), was used for *Agrobacterium* transformation.

Example 8

Synthetic Plant-Optimized Coding Region for SnRK2-6

A synthetic version of the coding sequence of an *Arabidopsis thaliana* SnRK2-6 gene was designed to enable production of the SnRK2-6 protein in transgenic dicot and monocot (e.g., maize) plants. The starting base sequence was Genbank Accession No. At4g33950, comprising a protein coding region as disclosed in SEQ ID NO:1, and encoding the protein sequence disclosed as SEQ ID NO:2.

To provide a plant-optimized DNA sequence encoding an SnRK2-6 protein, a DNA sequence was designed to encode the amino acid sequence of the protein, utilizing a redundant genetic code established from a codon bias table compiled from protein coding sequences of genes found in the particular host plants (maize and dicots). The protein coding regions of 706 maize genes (*Zea mays*) were extracted from Genbank, which is available from the National Center for Biotechnology Information, U.S. National Library of Medicine (Bethesda, Md.), and codon composition was calculated using the CodonFrequency function of the Wisconsin Sequence Analysis Package, available from Genetics Computer Group, University of Wisconsin (Madison, Wis.). Codon usage tables for tobacco (*Nicotiana tabacum;* 453,797 codons), cotton (*Gossypium hirsutum;* 62,111 codons), soybean (*Glycine max;* 362,096 codons), and canola (*Brassica napus;* 195,005 codons) are available from Kazusa DNA Research Institute (JAPAN).

TABLE 4A

Codon distributions in genes of maize and four dicot species.

| A<br>Amino<br>Acid | B<br>Codon | C<br>Plant<br>Weighted<br>Average<br>% | D<br>Plant<br>Average<br>% | E<br>Maize<br>Average<br>% | F<br>Dicot<br>Average<br>% | G<br>Cotton<br>% | H<br>Canola<br>% | I<br>Tobacco<br>% | J<br>Soybean<br>% |
|---|---|---|---|---|---|---|---|---|---|
| ALA (A) | GCA | 27.5 | 22.9 | 18 | 27.8 | 26.4 | 23.3 | 31.0 | 30.3 |
| | GCC | 33.0 | 27.4 | 34 | 20.9 | 22.6 | 21.2 | 17.3 | 22.5 |
| | GCG | DNU | DNU | 24 | 9.8 | 8.2 | 14.2 | 8.1 | 8.5 |
| | GCT | 39.5 | 33 | 24 | 41.6 | 42.8 | 41.3 | 43.6 | 38.7 |
| ARG (R) | AGA | 29.0 | 22.9 | 15 | 30.7 | 28.5 | 31.8 | 31.7 | 30.9 |
| | AGG | 32.5 | 25.6 | 26 | 25.3 | 26.8 | 22.1 | 24.6 | 27.6 |
| | CGA | DNU | DNU | 9 | 10.6 | 12.2 | 9.9 | 11.9 | 8.2 |
| | CGC | 21.3 | 16.8 | 24 | 9.5 | 8.5 | 8.9 | 8.1 | 12.7 |
| | CGG | DNU | DNU | 15 | 7.7 | 8.5 | 8.6 | 7.7 | 6.0 |
| | CGT | 17.2 | 13.6 | 11 | 16.2 | 15.6 | 18.6 | 16.0 | 14.5 |
| ASN (N) | AAC | 59.5 | 59.5 | 68 | 51.0 | 51.9 | 62.6 | 39.4 | 50.0 |
| | AAT | 40.5 | 40.5 | 32 | 49.0 | 48.1 | 37.4 | 60.6 | 50.0 |
| ASP (D) | GAC | 49.9 | 49.9 | 63 | 36.7 | 35.1 | 42.5 | 31.1 | 38.1 |
| | GAT | 50.1 | 50.1 | 37 | 63.3 | 64.9 | 57.5 | 68.9 | 61.9 |

TABLE 4A-continued

Codon distributions in genes of maize and four dicot species.

| A Amino Acid | B Codon | C Plant Weighted Average % | D Plant Average % | E Maize Average % | F Dicot Average % | G Cotton % | H Canola % | I Tobacco % | J Soybean % |
|---|---|---|---|---|---|---|---|---|---|
| CYS (C) | TGC | 58.4 | 58.4 | 68 | 48.7 | 53.1 | 49.2 | 42.6 | 50.0 |
|  | TGT | 41.6 | 41.6 | 32 | 51.3 | 46.9 | 50.8 | 57.4 | 50.0 |
| END | TAA | DNU | 30.1 | 20 | 40.2 | 39.1 | 38.5 | 42.6 | 40.7 |
|  | TAG | DNU | 21.1 | 21 | 21.2 | 20.3 | 22.1 | 19.6 | 22.7 |
|  | TGA | 100.0 | 48.8 | 59 | 38.6 | 40.6 | 39.4 | 37.8 | 36.6 |
| GLN (Q) | CAA | 46.7 | 46.7 | 38 | 55.5 | 57.4 | 50.0 | 58.9 | 55.5 |
|  | CAG | 53.3 | 53.3 | 62 | 44.5 | 42.6 | 50.0 | 41.1 | 44.5 |
| GLU (E) | GAA | 39.8 | 39.8 | 29 | 50.5 | 52.4 | 43.6 | 55.7 | 50.5 |
|  | CAG | 60.2 | 60.2 | 71 | 49.5 | 47.6 | 56.4 | 44.3 | 49.5 |
| GLY (G) | GGA | 26.1 | 26.1 | 19 | 33.2 | 29.9 | 36.4 | 34.6 | 31.9 |
|  | GGC | 29.8 | 29.8 | 42 | 17.5 | 18.3 | 16.2 | 16.2 | 19.3 |
|  | GGG | 18.0 | 18.0 | 19 | 17.0 | 19.0 | 15.2 | 15.4 | 18.4 |
|  | GGT | 26.1 | 26.1 | 20 | 32.3 | 32.7 | 32.1 | 33.7 | 30.4 |
| HIS (H) | CAC | 52.7 | 52.7 | 62 | 43.4 | 41.0 | 49.6 | 38.3 | 44.8 |
|  | CAT | 47.3 | 47.3 | 38 | 56.6 | 59.0 | 50.4 | 61.7 | 55.2 |
| ILE (I) | ATA | 18.3 | 18.3 | 14 | 22.7 | 20.4 | 21.1 | 25.8 | 23.4 |
|  | ATC | 45.7 | 45.7 | 58 | 33.3 | 36.1 | 42.7 | 24.6 | 29.9 |
|  | ATT | 36.0 | 36.0 | 28 | 44.0 | 43.5 | 36.2 | 49.6 | 46.7 |

TABLE 4B

Codon distributions in genes of maize and four dicot species.

| A Amino Acid | B Codon | C Weighted Average % | Plant Average % | E Maize % | F Dicot Average % | G Cotton % | H Canola % | I Tobacco % | J Soybean % |
|---|---|---|---|---|---|---|---|---|---|
| LEU (L) | CTA | DNU | DNU | 8 | 9.4 | 7.8 | 10.1 | 10.5 | 9.1 |
|  | CTC | 26.3 | 21.8 | 26 | 17.7 | 16.7 | 22.8 | 13.0 | 18.1 |
|  | CTG | 24.7 | 20.5 | 29 | 12.0 | 12.0 | 11.6 | 11.2 | 13.2 |
|  | CTT | 26.0 | 21.6 | 17 | 26.1 | 27.9 | 25.2 | 25.9 | 25.5 |
|  | TTA | DNU | DNU | 5 | 11.4 | 10.5 | 10.1 | 15.3 | 9.8 |
|  | TTG | 23.1 | 19.2 | 15 | 23.4 | 25.1 | 20.2 | 24.0 | 24.2 |
| LYS (K) | AAA | 33.5 | 33.5 | 22 | 45.1 | 43.1 | 44.6 | 50.0 | 42.5 |
|  | AAG | 66.5 | 66.5 | 78 | 54.9 | 56.9 | 55.4 | 50.0 | 57.5 |
| MET (M) | ATG | 100.0 | 100.0 | 100 | 100 | 100.0 | 100.0 | 100.0 | 100.0 |
| PHE (F) | TTC | 61.0 | 61.0 | 71 | 51.0 | 54.3 | 58.6 | 41.9 | 49.2 |
|  | TTT | 39.0 | 39.0 | 29 | 49.0 | 45.7 | 41.4 | 58.1 | 50.8 |
| PRO (P) | CCA | 30.4 | 30.4 | 26 | 34.8 | 34.0 | 29.6 | 38.9 | 36.5 |
|  | CCC | 20.0 | 20.0 | 24 | 16.0 | 16.6 | 14.6 | 13.6 | 19.2 |
|  | CCG | 20.0 | 20.0 | 28 | 12.0 | 11.1 | 18.4 | 10.0 | 8.3 |
|  | CCT | 29.6 | 29.6 | 22 | 37.3 | 38.2 | 37.3 | 37.5 | 36.0 |
| SER (S) | AGC | 24.9 | 19.0 | 23 | 15.0 | 16.4 | 16.0 | 12.5 | 15.1 |
|  | AGT | DNU | DNU | 9 | 15.9 | 15.2 | 14.1 | 17.3 | 17.1 |
|  | TCA | 23.6 | 18.0 | 16 | 20.1 | 18.9 | 18.2 | 22.6 | 20.6 |
|  | TCC | 25.8 | 19.7 | 23 | 16.4 | 17.8 | 16.7 | 14.1 | 16.9 |
|  | TCG | DNU | DNU | 14 | 8.4 | 9.5 | 10.7 | 7.2 | 6.1 |
|  | TCT | 25.7 | 19.6 | 15 | 24.2 | 22.1 | 24.3 | 26.2 | 24.2 |
| THR (T) | ACA | 25.2 | 25.2 | 21 | 29.4 | 28.9 | 26.3 | 32.7 | 29.7 |
|  | ACC | 31.1 | 31.1 | 37 | 25.3 | 27.6 | 26.9 | 19.1 | 27.7 |
|  | ACG | 16.7 | 16.7 | 22 | 11.3 | 11.4 | 16.9 | 8.8 | 8.3 |
|  | ACT | 27.0 | 27.0 | 20 | 34.0 | 32.2 | 30.0 | 39.4 | 34.3 |
| TRP (W) | TGG | 100.0 | 100.0 | 100 | 100 | 100.0 | 100.0 | 100.0 | 100.0 |

TABLE 4B-continued

Codon distributions in genes of maize and four dicot species.

| A<br>Amino<br>Acid | B<br>Codon | C<br>Weighted<br>Average<br>% | Plant<br>Average<br>% | E<br>Maize<br>% | F<br>Average<br>% | G<br>Cotton<br>% | H<br>Canola<br>% | I<br>Tobacco<br>% | J<br>Soybean<br>% |
|---|---|---|---|---|---|---|---|---|---|
| TYR (Y) | TAC | 61.3 | 61.3 | 73 | 49.6 | 49.4 | 59.4 | 41.4 | 48.2 |
|  | TAT | 38.7 | 38.7 | 27 | 50.4 | 50.6 | 40.6 | 58.6 | 51.8 |
| VAL (V) | GTA | DNU | DNU | 8 | 13.0 | 11.5 | 10.8 | 18.3 | 11.5 |
|  | GTC | 28.9 | 25.9 | 32 | 19.8 | 20.2 | 24.1 | 17.0 | 17.8 |
|  | GTG | 37.3 | 33.4 | 39 | 27.8 | 26.7 | 28.3 | 24.3 | 32.0 |
|  | GTT | 33.7 | 30.2 | 21 | 39.4 | 41.5 | 36.8 | 40.4 | 38.7 |

Native gene codon usages for maize genes are shown in Tables 4A and 4B, Columns E, and those for the dicots genes are shown in Tables 4A and 4B, Columns G-J. The values in Columns E and G-J present the distributions (in % of usage for all codons for that amino acid) of synonymous codons for each amino acid. The codons most preferred by each plant type are indicated in bold font, and the second, third, or fourth, etc, choices of codons can be identified when multiple choices exist. It is evident that some synonymous codons for some amino acids are found only rarely in dicot genes (e.g., CGG and TCG). Also, some dicot plants differ somewhat in codon preference for particular amino acids (e.g., Asparagine and Phenylalanine codons). It is also evident that some synonymous codons for some amino acids are found only rarely in plant protein coding regions (e.g., CGA and CTA). Further, maize and dicot plants differ in codon usage (e.g., Alanine codon GCC occurs more frequently in maize genes than in dicot genes, while Alanine codon GCT is more often used in dicot genes than in maize genes). Thus, it is obvious that a protein coding region designed to reflect the optimal codon composition of genes of one plant group may have a suboptimal codon composition for expression in another plant group. To derive a biased codon set that comprises the most-highly used codons common to maize and dicots, an average for each codon was calculated for the dicot plant dataset shown in Column F of Tables 4A and 4B.

The average % distribution value for each codon in maize and dicot genes was calculated from the data in Tables 4A and 4B, Columns E and F, and is presented as the Plant Average in Tables 4A and 4B, Column D. Usually, the % usage values of a codon considered to be rarely used (i.e., represented at about 10% or less of the time to encode the relevant amino acid in genes of either maize or dicot plants) were not included in the analysis. These codon values are indicated by DNU (Do Not Use) in Tables 4A and 4B, Column D. In those instances, the total % codon usage values for the individual amino acids do not total 100% in Tables 4A and 4B, Column D.

To balance the distribution of the remaining codon choices for those amino acids, a Weighted Average % representation for each codon was calculated, using the formula:

Weighted Average % of $C1=1/(\% \ C1+\% \ C2+\% \ C3+etc.)\times\% \ C1\times100$, where C1 is the codon in question and % C2, % C3, etc., represent the Plant Average % values for the remaining synonymous codons, as shown in Column D of Tables 4A and 4B.

The Plant Weighted Average % distributions of codons calculated for maize and dicots genes are presented in Tables 4A and 4B, Column C. Thus, the codon identities of Columns B, taken together with the % distribution values in Columns C, comprise a Plant-Optimized Codon Bias Table calculated from genes of maize, cotton, canola, tobacco, and soybean. A Plant-Optimized gene will be determined to have an overall codon distribution similar to the codon distribution in Tables 4A and 4B, Columns C.

To engineer a Plant-Optimized sequence encoding an SnRK2-6 protein, a DNA sequence was designed to encode the amino acid sequence of the protein, utilizing a redundant Plant Optimized Codon Bias Table compiled from the protein coding sequences of dicots and maize. The native SnRK2-6 DNA sequence (SEQ ID NO:1) was translated into the deduced amino sequence of the SnRK2-6 protein (SEQ ID NO:2), then the protein sequence was reverse-translated into a Plant-Optimized DNA sequence using the OptGene™ program, which is commercially available from Ocimum Biosolutions (Indianapolis, Ind.). Further refinements of the sequence were made to eliminate undesirable restriction enzyme recognition sites, potential plant intron splice sites, long runs of A/T or C/G residues, and other motifs that might interfere with RNA stability, transcription, or translation of the coding region in plant cells. Other changes were made to introduce desired restriction enzyme recognition sites, and to eliminate long internal Open Reading Frames (frames other than +1) and unusually stable stemloops structures. These changes were all made within the constraints of retaining the Plant-Optimized biased codon composition as described above. The Plant-Optimized sequence encoding the SnRK2-6 protein is designated SnRK2-6 hv5, and the sequence is disclosed as SEQ ID NO:3, encoding SEQ ID NO:2.

Table 5 compares the codon compositions of the Plant-Optimized SnRK2-6 hv5 coding region with the Plant-Optimized Codon Biased table, thus demonstrating the result of the optimization process.

TABLE 5

Comparison of Codon Compositions of native SnRK2-6 coding region, Plant-Optimized version hv5, and the Plant-Optimized Codon Bias Composition

| Amino<br>Acid | Codon | Native<br>SnRK2-6<br>% | Optimized<br>SnRK2-6<br>hv5% | Plant<br>Optimized<br>Average |
|---|---|---|---|---|
| ALA (A) | GCA | 52.4 | 28.6 | 27.5 |
|  | GCC | 9.5 | 33.3 | 33.0 |
|  | GCG | 9.5 | 0.0 | DNU |
|  | GCT | 28.6 | 38.1 | 39.5 |
| ARG (R) | AGA | 35.0 | 30.0 | 29.0 |
|  | AGG | 35.0 | 30.0 | 32.5 |
|  | CGA | 15.0 | 0.0 | DNU |
|  | CGC | 10.0 | 20.0 | 21.3 |
|  | CGG | 0.0 | 0.0 | DNU |
|  | CGT | 5.0 | 20.0 | 17.2 |

TABLE 5-continued

Comparison of Codon Compositions
of native SnRK2-6 coding region,
Plant-Optimized version hv5, and the
Plant-Optimized Codon Bias Composition

| Amino Acid | Codon | Native SnRK2-6 % | Optimized SnRK2-6 hv5% | Plant Optimized Average |
|---|---|---|---|---|
| ASN (N) | AAC | 33.3 | 60.0 | 59.5 |
|  | AAT | 66.7 | 40.0 | 40.5 |
| ASP (D) | GAC | 33.3 | 53.3 | 49.9 |
|  | GAT | 66.7 | 46.7 | 50.1 |
| CYS (C) | TGC | 16.7 | 66.7 | 58.4 |
|  | TGT | 83.3 | 33.3 | 41.6 |
| END | TAA | 0.0 | 0.0 | DNU |
|  | TAG | 0.0 | 0.0 | DNU |
|  | TGA | 100.0 | 100.0 | 100.0 |
| GLN (Q) | CAA | 54.5 | 45.5 | 46.7 |
|  | CAG | 45.5 | 54.5 | 53.3 |
| GLU (E) | GAA | 55.2 | 37.9 | 39.8 |
|  | GAG | 44.8 | 62.1 | 60.2 |
| GLY (G) | GGA | 52.6 | 26.3 | 26.1 |
|  | GGC | 21.1 | 31.6 | 29.8 |
|  | GGG | 5.3 | 15.8 | 18.0 |
|  | GGT | 21.1 | 26.3 | 26.1 |
| HIS (H) | CAC | 33.3 | 58.3 | 52.7 |
|  | CAT | 66.7 | 41.7 | 47.3 |
| ILE (I) | ATA | 37.9 | 17.2 | 18.3 |
|  | ATC | 31.0 | 48.3 | 45.7 |
|  | ATT | 31.0 | 34.5 | 36.0 |
| LEU (L) | CTA | 16.7 | 0.0 | DNU |
|  | CTC | 13.3 | 33.3 | 26.3 |
|  | CTG | 13.3 | 0.0 | 24.7 |
|  | CTT | 13.3 | 33.3 | 26.0 |
|  | TTA | 30.0 | 0.0 | DNU |
|  | TTG | 13.3 | 33.3 | 23.1 |
| LYS (K) | AAA | 35.3 | 29.4 | 33.5 |
|  | AAG | 64.7 | 70.6 | 66.5 |
| MET (M) | ATG | 100 | 100 | 100.0 |
| PHE (F) | TTC | 61.5 | 61.5 | 61.0 |
|  | TTT | 38.5 | 38.5 | 39.0 |
| PRO (P) | CCA | 23.8 | 42.9 | 30.4 |
|  | CCC | 9.5 | 23.8 | 20.0 |
|  | CCG | 23.8 | 0.0 | 20.0 |
|  | CCT | 42.9 | 33.3 | 29.6 |
| SER (S) | AGC | 24.0 | 24.0 | 24.9 |
|  | AGT | 20.0 | 0.0 | DNU |
|  | TCA | 20.0 | 16.0 | 23.6 |
|  | TCC | 12.0 | 28.0 | 25.8 |
|  | TCG | 8.0 | 0.0 | DNU |
|  | TCT | 16.0 | 32.0 | 25.7 |
| THR (T) | ACA | 15.4 | 30.8 | 25.2 |
|  | ACC | 15.4 | 38.5 | 31.1 |
|  | ACG | 15.4 | 0.0 | 16.7 |
|  | ACT | 53.8 | 30.8 | 27.0 |
| TRP (W) | TGG | 100 | 100 | 100.0 |
| TYR (Y) | TAC | 30.8 | 61.5 | 61.3 |
|  | TAT | 69.2 | 38.5 | 38.7 |
| VAL (V) | GTA | 8.3 | 0.0 | DNU |
|  | GTC | 8.3 | 29.2 | 28.9 |
|  | GTG | 12.5 | 37.5 | 37.3 |
|  | GTT | 70.8 | 33.3 | 33.7 |

To complete the design, a 5' Untranslated Sequence containing translational Stop codons in all three top strand reading frames, and initiated by a recognition sequence for Bbs I restriction enzyme, was added to the 5' end of the SnRK2-6 hv5 sequence. Additionally, a 3' Untranslated Sequence containing translational Stop codons in all six open reading frames, and terminated by the recognition sequence for Sac I restriction enzyme, was added to the 3' end of the SnRK2-6 hv5 sequence. This sequence, called SnRK2-6 hv6, is disclosed as SEQ ID NO:4. Synthesis of the SnRK2-6 hv6 designed sequence was contracted to PicoScript in Houston, Tex.

Example 9

Construction of SnRK2-6 Expression Vector for Corn Transformation

To heterologously express SnRK2-6 gene in corn, its open reading frame sequence was codon optimized according to hemicot codon usage, thus designated SnRK2-6 Additionally, the nucleotide sequences corresponding to "3-frame stops" and "maize consensus" were introduced to 5'-terminus of the SnRK2-6 hv gene, and "6-frame stops" to its 3'-terminus. To facilitate subsequent cloning, two restriction sites, Bbs I and Sac I, were added to 5'- and 3'-end of the sequence. Then, the entire sequence was synthesized, which is described in further detail below.

Figure 12:
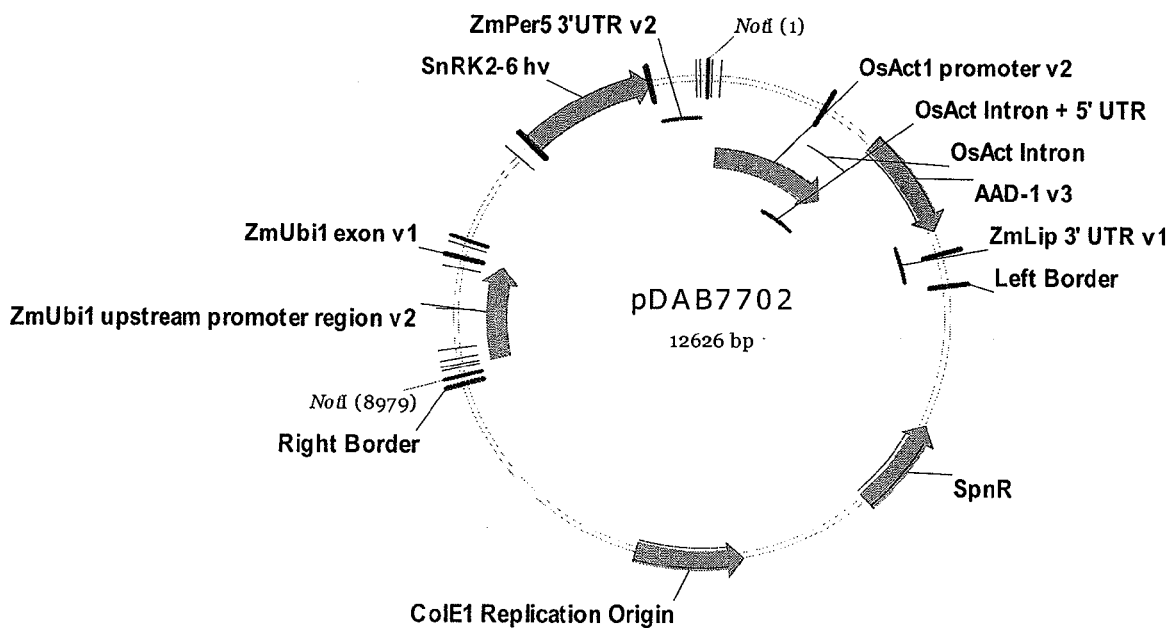
FIG. 12 is a map of plasmid pDAB7702, which may be used as a vector. The vector contains the following salient features for plant transformation in the current invention: the maize Ubi1 promotor, SnRK2-6 hv, and ZmPerS 3'UTR.

The above synthesized fragment digested with Bbs I and Sac I was inserted into Acc65 I- and Sac I-digested pDAB4005. This created a plant transcription unit (PTU) containing maize Ubi1 promoter, SnRK2-6 hv and ZmPer5 3'UTR. The PTU was excised from the recombinant pDAB4005 through digestion with Not I and inserted into the destination vector pDAB3878. The orientation and integrity of the resulting plasmid, designated pDAB7702, which is shown in FIG. 12, was determined by sequencing.

Example 10

*Agrobacterium* and *Arabidopsis* Transformation

The transformation was conducted as described by Weigel and Glazebrook (2002).

*Arabidopsis thaliana* Growth Conditions

Freshly harvested seed was allowed to dry for 7 days at room temperature in the presence of desiccant. Seed was suspended in a 0.1% Agarose solution, which is commercially available from Sigma Chemical Co. (St. Louis, Mo.). The suspended seed was stored at 4° C. for two days to complete dormancy requirements and ensure synchronous seed germination (stratification).

Sunshine Mix LP5, which is commercially available from Sun Gro Horticulture Inc. (Bellevue, Wash.) was covered with fine vermiculite and sub-irrigated with Hoaglan's solution until wet. The soil mix was allowed to drain for 24 hours. Stratified seed was sown onto the vermiculite and covered with humidity domes, such as those commercially available from KORD Products (Bramalea, Ontario, Canada) for five to seven days.

Seeds were germinated and plants were grown in a Conviron (models CMP4030 and CMP3244), which are commercially available from Controlled Environments Limited (Winnipeg, Manitoba, Canada) under long day conditions (16 hours light/8 hours dark) at a light intensity in a range of from about 120 µmol/m2 sec to about 150 µmol/m2 sec under constant temperature of about 22° C. and a humidity in a range of from about 40% to about 50%. Plants were initially watered with Hoaglan's solution and subsequently with DI water to keep the soil moist but not wet.

*Agrobacterium* Transformation

Electro-competent *Agrobacterium tumefaciens* (strain Z707S) cells were prepared using a protocol from Weigel and Glazebrook (2002). The competent agro cells were transformed using an electroporation method adapted from Weigel and Glazebrook (2002). Fifty (50) µl of competent agro cells were thawed on ice and about 10 nm to about 25 ng of the plasmid pDAB4504 was added to the cells. The DNA and cell mix was added to pre-chilled 2 mm electroporation cuvettes. An Eppendorf Electroporator 2510, which is commercially available from Eppendorf AG (Hamburg, Germany), was used for the transformation at the following settings: Voltage: 2.4 kV, Pulse length: 5 msec. After electroporation, 1 mL of YEP broth was added to the cuvette and the cell-YEP suspension was transferred to a 15 ml culture tube. The cells were incubated at 28° C. in a water bath with constant agitation for four hours. After incubation, the culture was plated on YEP+ agar with spectinomycin (100 mg/L) and streptomycin (250 mg/L), which are commercially available from Sigma Chemical Co. (St. Louis, Mo.). The plates were incubated for 2-4 days at 28° C. Colonies were selected and streaked onto fresh YEP +agar with spectinomycin (100 mg/L) and streptomycin (250 mg/L) plates and incubated at about 28° C. for one to three days. Colonies were selected for restriction digest analysis to verify the presence of the gene insert by using vector specific restriction digest enzymes. Qiagen High Speed Maxi Preps, performed per manufacturer's instructions, were used to purify the plasmid DNA from selected *Agrobacterium* colonies. Plasmid DNA from the binary vector used in the *Agrobacterium* transformation was included as a control. Four separate digest reactions were run using 0.5-1 µg of DNA. The reaction was allowed to run for about four hours to about five hours and was analyzed by 0.65% agarose gel electrophoresis and visualized by ethidium bromide staining. A colony was selected whose digest for all enzymes was identical to the plasmid control.

*Arabidopsis* Transformation

*Arabidopsis* was transformed using the floral dip method. The selected colony was used to inoculate one or more 15 mL pre-cultures of YEP broth containing spectinomycin (100 mg/L) and streptomycin (250 mg/L). The culture(s) was incubated overnight at about 28° C. with constant agitation at 220 rpm. Each pre-culture was used to inoculate two, 500 ml cultures of YEP broth containing spectinomycin (100 mg/L) and streptomycin (250 mg/L) and the cultures were incubated overnight at about 28° C. with constant agitation. The cells were then pelleted at about 8700×g for about ten minutes at room temperature (i.e., about 24° C.), and the resulting supernatant discarded. The cell pellet was gently resuspended in 500 mL infiltration media containing: ½× Murashige and Skoog salts and Gamborg's B5 vitamins, 10% (w/v) sucrose, 0.044 µM benzylamino purine (10 µl/liter of 1 mg/ml stock in DMSO) and 300 µl/liter SILWET L-77, which is commercially available from Helena Chemical Company (Collierville, Tenn.). Plants about five weeks old were dipped into the media for about 15 seconds, being sure to submerge the newest inflorescence. The plants were then lay down on their sides and covered (transparent or opaque) for about 24 hours, then washed with water, and placed upright. The plants were grown at about 22° C., with a 16-hour light/8-hour dark photoperiod. About four weeks after dipping, the seeds were harvested.

Selection of Transformed Plants

T1 seed was sown on 10.5"×21" germination trays, which are commercially available from T.O. Plastics Inc. (Clearwater, Minn.) as described and grown under the conditions outlined. The domes were removed five to six days post sowing. Five days post-sowing and again ten days post-sowing seedlings were sprayed with a 0.20% solution (20 µl/10 mL deionized water) of glufosinate herbicide, which is commercially available from Bayer Cropscience, in a spray volume of about 10 ml/tray (703 L/ha) using a DeVilbiss compressed air spray tip (Glendale Heights, Ill.) to deliver an effective rate of 280 g/ha glufosinate per application. The amount of Liberty to prepare was calculated as follows: (703 L/ha spray volume=280 GPA). (280 g ai/ha)×(1 ha/703L)×(1 L/200 g ai glufosinate)=0.20% solution (i.e., 20 µl/10 ml). Ten (10) mL of the solution was pipetted into a 20 mL scintillation vial for each tray to be sprayed. The spray was delivered using a horizontal and vertical application pattern. After each spray, a spray label with the herbicide name, application rate and application date was added to each selection tray. Four to seven days after the second spray herbicide resistant plants were identified and transplanted into pots prepared with Sunshine mix LP5. Transplanted plants were placed in a conviron with the above mentioned growth conditions.

Example 11

*Agrobacterium* Transformation for Superbinary Vectors

To prepare for transformation, two different *E. coli* strains (DH5α containing the pSB11 precursor {either pDAB7702 or pDAB3878 in this case} and pRK2013) were grown at 37° C. overnight. The DH5α strain was grown on a petri plate containing LB (5 g Bacto Tryptone, 2.5 g Bacto Yeast Extract, 5 g NaCl, 7.5 g Agar, in 500 ml deionized water)+Spectinomycin (100 µg/ml) and the pRK2013 strain was grown on a petri plate containing LB+Kanamycin (50 µg/ml). After incubation the plates were placed at about 4° C. to await the availability of the *Agrobacterium*.

*Agrobacterium* strain LBA4404 containing pSB1 (Japan Tobacco) was grown on a petri plate containing AB medium (5 g Glucose, 15 g Agar, in 900 ml deionized water) with Streptomycin (250 µg/ml) and Tetracycline (10 µg/ml) at 28° C. for three days. After the *Agrobacterium* was ready, transformation plates were set up by mixing one inoculating loop of each bacteria (pDAB7702 or pDAB3878, pRK2013, and LBA4404+pSB1) on a LB plate with no antibiotics. This plate was incubated at 28° C. overnight. After incubation 1 ml of 0.9% NaCl (4.5 g NaCl in 500 ml deionized water) solution was added to the mating plate and the cells were mixed into the solution. The mixture was then transferred into a labeled sterile tube, such a Falcon 2059, which is commercially available from Becton Dickinson and Co. (Franklin Lakes, N.J.).

One (1) ml of 0.9% NaCl was added to the plate and the remaining cells were mixed into the solution. This mixture was then transferred to the same labeled tube as above. Serial dilutions of the bacterial cells were made ranging from $10^1$-$10^4$ by placing 100 μl of the bacterial "stock" solution into labeled Falcon 2059 tubes and then adding 900 μl of 0.9% NaCl. To ensure selection, 100 μl of the dilutions were then plated onto separate AB+Spectinomycin (100 μg/ml)/Streptomycin (250 μg/ml)/Tetracycline (10 μg/ml) and incubated at 28° C. for four days. The colonies were then "patched" onto AB+Spec/Strep/Tet plates as well as lactose medium (0.5 g Yeast Extract, 5 g D-lactose monohydrate, 7.5 g Agar, in 500 ml DI $H_2O$) plates and placed in the incubator at 28° C. for two days. A Keto-lactose test was performed on the colonies on the lactose media by flooding the plate with Benedict's solution (86.5 g Sodium Citrate monobasic, 50 g $Na_2CO_3$, 9 g $CuSO_4$-5 water, in 500 ml of deionized water) and allowing the agro colonies to turn yellow. Any colonies that were yellow (positive for agro) were then picked from the patch plate and streaked for single colony isolation on AB+Spec/Strep/Tet plates at 28° C. for two days. One colony per plate was picked for a second round of single colony isolations on AB+Spec/Strep/Tet media and this was repeated for a total of three rounds of single colony isolations. After the isolations, one colony per plate was picked and used to inoculate separate 3 ml YEP (5 g Yeast Extract, 5 g Peptone, 2.5 g NaCl, in 500 ml deionized water) liquid cultures containing Spectinomycin (100 μg/ml), Streptomycin (250 μg/ml), and Tetracycline (10 μg/ml). These liquid cultures were then grown overnight at 28° C. in a drum incubator at 200 rpm.

Validation cultures were then stated by transferring 2 ml of the inoculation cultures to 250 ml disposable flasks containing 75 ml of YEP+Spec/Strep/Tet. These were then grown overnight at 28° C. while shaking at 200 rpm. Following the Qiagen® protocol, Hi-Speed maxi-preps, commercially available from Qiagen (Valencia, Calif.), were then performed on the bacterial cultures to produce plasmid DNA. 500 μl of the eluted DNA was then transferred to two clean, labeled 1.5 ml tubes and the Quick-Precip Plus® protocol, which is commercially available from Edge BioSystems (Gaithersburg, Md.), was performed. After the precipitation the DNA was resuspended in a total volume of 100 μl TE, including a mixture of 10 mM Tris HCl at pH 8.0 and 1 mM ethylene diamine tetraacetic acid (EDTA). Five (5) μl of plasmid DNA was added to and gently mixed with 50 μl of chemically competent DH5α $E.$ $coli$ cells, commercially available from Invitrogen (Carlsbad, Calif.).

This mixture was then transferred to chilled and labeled Falcon 2059 tubes. The reaction was incubated on ice for about 30 minutes and then "Heat shocked" by increasing the temperature to about 42° C. for about 45 seconds. The reaction was placed back into the ice for about two minutes and then 450 μl of SOC medium, which is commercially available from Invitrogen (Carlsbad, Calif.), was added to the tubes. The reaction was then incubated at 37° C. for one hour, shaking at 200 rpm. The cells were then plated onto LB+Spec/Strep/Tet (using 50 μl and 100 μl) and incubated at 37° C. overnight. Three or four colonies per plate were picked and used to inoculate separate 3 ml LB (5 g Bacto Tryptone, 2.5 g Bacto Yeast Extract, 5 g NaCl, in 500 ml DI $H_2O$) liquid cultures containing Spectinomycin (100 μg/ml), Streptomycin (250 μg/ml), and Tetracycline (10 μl/ml). These liquid cultures were then grown overnight at 37° C. in a drum incubator at 200 rpm. Following the Qiagen® protocol, mini-preps (Qiagen, Valencia, Calif.) were then performed on the bacterial cultures to produce plasmid DNA. Five (5) μl of plasmid DNA was then digested in separate reactions using HindIII and SalI enzymes (New England Biolabs Beverly, Mass.) at 37° C. for one hour before being ran on a 1% agarose (Cambrex Bio science Rockland, Inc. Rockland, Me.) gel.

The culture that showed the correct banding pattern was then used to create glycerol stocks by adding 500 μl of culture to 500 μl of sterile glycerol (Sigma Chemical Co.; St. Louis, Mo.) and inverting to mix. The mixture was then frozen on dry ice and stored at −80° C. until needed.

Example 12

*Agrobacterium*-Mediated Transformation of Maize

Plant Material

Seeds from a High II $F_1$ cross (Armstrong et al., 1991) were planted into five-gallon pots containing a mixture of 95% Metro-Mix 360 soilless growing medium (Sun Gro Horticulture, Bellevue, Wash.) and 5% clay/loam soil. The plants were grown in a greenhouse using a combination of high pressure sodium and metal halide lamps with a 16:8 hour photoperiod. For obtaining immature $F_2$ embryos for transformation, controlled sib-pollinations were performed. Immature embryos were isolated at eight to ten days post-pollination when embryos were approximately 1.0 to 2.0 mm in size.

Infection and Cocultivation

Maize ears were surface sterilized by scrubbing with liquid soap, immersing in 70% ethanol for two minutes, and then immersing in 20% commercial bleach (0.1% sodium hypochlorite) for 30 minutes before being rinsed with sterile water. The *Agrobacterium* suspension was prepared by transferring one to two loops of bacteria grown on YEP medium (40 g/L peptone, 40 g/L yeast extract, 20 g/L NaCl, 15 g/L Bacto agar) containing 100 mg/L spectinomycin, 10 mg/L tetracycline, and 250 mg/L streptomycin at 28° C. for two to three days into 5 mL of liquid infection medium (LS Basal Medium (Linsmaier and Skoog, 1965), N6 vitamins (Chu et al., 1965), 1.5 mg/L 2,4-D, 68.5 g/L sucrose, 36.0 g/L glucose, 6 mM L-proline, pH 5.2) containing 100 μM acetosyringone. The solution was vortexed until a uniform suspension was achieved, and the concentration was adjusted to a final density of 200 Klett units, using a Klett-Summerson colorimeter with a purple filter. Immature embryos were isolated directly into a micro centrifuge tube containing 2 mL of the infection medium. Tubes were vortexed for three to five seconds, then the liquid medium was removed and replaced with fresh medium and vortexed again. The medium was removed a third time and replaced with 1 mL of the *Agrobacterium* solution with a density of 200 Klett units. The *Agrobacterium* and embryo solution was vortexed at maximum speed for 30 seconds, then incubated for five minutes at room temperature, before being transferred to co-cultivation medium (LS Basal Medium, N6 vitamins, 1.5 mg/L 2,4-D, 30.0 g/L sucrose, 6 mM L-proline, 0.85 mg/L $AgNO_3$, 1, 100 μM acetosyringone, 3.0 g/L Gellan gum, pH 5.8) for five days at 25° C. under dark conditions.

After co-cultivation, the embryos were moved through a two-step selection scheme after which transformed isolates were obtained over the course of approximately eight weeks. For selection, and LS based medium (LS Basal medium, N6 vitamins, 1.5 mg/L 2,4-D, 0.5 g/L MES, 30.0 g/L sucrose, 6 mM L-proline, 1.0 mg/L $AgNO_3$, 250 mg/L cephotaxime, 2.5 g/L Gellan gum, pH 5.7) was used with multiple selection levels of R-haloxyfop acid. The embryos were transferred to selection media containing 100 nM R-haloxyfop for 14 days, and then transferred to 500 nM R-haloxyfop at biweekly intervals about three more times until embryogenic isolates were obtained. Any recovered isolates were bulked up by transferring to fresh selection medium at two-week intervals for regeneration and further analysis.

Regeneration and Seed Production

For regeneration, the cultures were transferred to "28" induction medium (MS salts and vitamins, 30 g/L sucrose, 5 mg/L benzylaminopurine, 0.25 mg/L 2, 4-D, 100 nM R-haloxyfop acid, 250 mg/L cephotaxime, 2.5 g/L Gellan gum, pH 5.7) for one week under low-light conditions (14 µEm$^{-2}$s$^{-1}$) then 1 week under high-light conditions (approximately 89 µEm$^{-2}$s$^{-1}$). Tissues were subsequently transferred to "36" regeneration medium (same as induction medium except lacking plant growth regulators). When plantlets grew to 3-5 cm in length, they were transferred to glass culture tubes containing SHGA medium (Schenk and Hildebrandt salts and vitamins (1972)), 1.0 g/L myo-inositol, 10 g/L sucrose and 2.0 g/L Gellan gum, pH 5.8) to allow for further growth and development of the shoot and roots. Plants were transplanted to the same soil mixture as described earlier herein and grown to flowering in the greenhouse. Controlled pollinations for seed production were conducted.

Example 13

Molecular Characterization of SnRK2-6 Transgenic *Arabidopsis*

To screen transgenic *Arabidopsis* plants carrying the transcription unit of SnRK2-6, PCR was conducted with a pair of primers, 5'-TGA GGT CTA CAG GCC AAA TTC GCT CTT AGC-3' (SEQ ID NO:39) and 5'-ATC ACA TTG CGT ACA CAA TCT CT-3' (SEQ ID NO:40), designed according to the sequence near T-DNA left border and 3'-end sequence of SnRK2-6, respectively. Genetic segregation of T2 transgenic plants was determined using PAT invader assay and herbicide spraying. Only those transgenic lines fit to 3:1 segregation were selected for biochemical and physiollogical studies as they are very like to carry single insertion.

Example 14

Molecular Characterization of SnRK2-6 hv Transgenic Corn

To screen transgenic corn plants carrying the transcription unit of SnRK2-6 hv, PCR was conducted with a pair of primers, 5'-GTG ACC CGG TCG TGC CCC TCT CTA GA-3' (SEQ ID NO:41) and 5'-CCG TGG ATA TAT GCC GTG AAC AAT TG-3' (SEQ ID NO:42), designed according to ZmUbi1 promoter and ZmPer5 3'UTR, respectively.

Example 15

Western Blot Analysis

Preparation of Polyclonal Antibodies
Two different kinds of polyclonal antibodies were prepared against two polypeptides, "CHRDLKLENTLLDGSPA-PRLKICDFGYSKS" (30 amino acids) (SEQ ID NO:43) and "MNDNTMTTQFDESDQPGQSIEE" (22 amino acids) (SEQ ID NO:44), respectively. The first polypeptide is located at the amino acid positions from 137 to 166 in the kinase domain of SnRK2-6 protein, and the second peptide is located at the amino acid positions from 286 to 307 in the regulatory domain of SnRK2-6 protein. These two polypeptides were synthesized and conjugated to keyhole limpet hemocyanin (KLH) as carrier protein. The resulting two different peptide-KLH conjugates were used for rabbit immunization to generate two different kinds of polyclonal antibodies. To purify the antibodies, the peptides were conjugated to bovine serum albumin (BSA), and the conjugates used for affinity chromatography.

Sample Preparation
The corn leaves from SNF1 kinase transformed plants and controls were sampled with dry ice and ground with liquid nitrogen to very fine powder. The proteins including the SNF1 kinase were extracted by adding ~200 mg of the leaf powder in 1 mL of extract buffer (50 mM Tris, pH 8.0, 50 mM NaCl, 5 mM EDTA, 5 mM DTT, 0.05% Triton X-100). The protein concentrations of the extracts were measured by Bio-Rad protein assay and they varied from 3.2-3.8mg/mL.

Western Blot
The proteins were separated by SDS-PAGE using a Nupage 10% Bis-Tris gel, which is commercially available from Invitrogen, cat#NP0301Box (Carlsbad, Calif.) with MOPS running buffer. Then they were transferred onto nitrocellulose membrane with Tris/glycine buffer for one hour at 100 V. The membrane was blocked in PBST buffer containing 3% no-fat milk for one hour at room temperature (RT). The milk solution was poured off and fresh buffer containing the rabbit anti-SnRK2-6 polyclonal antibodies was added. The membrane was incubated one hour at RT, and then washed three times with PBST. After washing, fresh PBST/milk solution containing the goat anti-rabbit IgG-horseradish peroxidase conjugate was added to the membrane. After incubation for one hour at RT, the membrane was washed as described previously. For development, the membrane was removed from the PBST solution and immersed in freshly prepared ECL detection reagent (PIERCE, detection reagent 1—peroxide solution, Cal #1859701, and detection reagent 2—luminol enhancer solution, Cal #1859698). Chemiluminescence film (CL-Xposure Film, from PIERCE, cal #31460) was exposed to the treated membrane and developed with the Konica SR-X film developer.

Example 16

Heterologous Expression of SnRK2-6 Increases Corn Drought Tolerance

To test if SnRK2-6 kinase can exert the effect on biological processes in heterologous chromosomal backgrounds, we expressed the SnRK2-6 gene in corn. To establish its function, the gene sequence was codon-optimized according to hemicotyledon codon usage and then introduced into Hi II corn under the control of maize Ubi1 promoter. The expression of SnRK2-6 in corn transgenic lines was determined using Western blot based on polyclonal antibodies against SnRK2-6 peptides. The expressed protein had the expected size (42 kD), and showed the level readily detectable in the majority of the lines by Western blot. As control, non-transformant Hi II plants did not show a detectable level of any proteins at 42 kD (data not shown).

$T_0$ Hi II transgenic corn plants were reciprocally crossed with the inbred line 5XH751 to produce T1 seeds. The resulting T1 segregation populations were screened by PCR to separate null segregants and plants carrying the transgene. In the experiments designed to test drought tolerance, null segregants serve as control for those transgenic plants segregated from the same population because their genomic backgrounds are most similar to each other.

Figure 8:
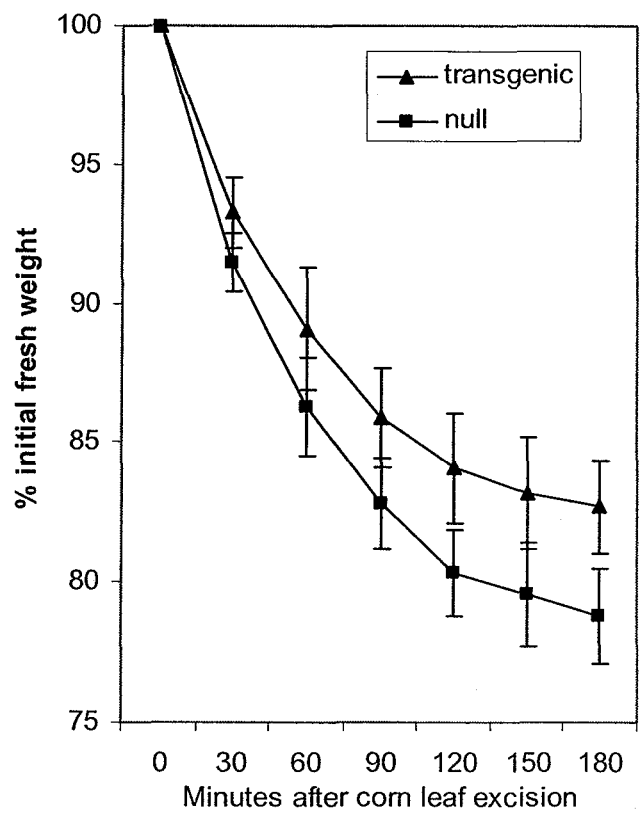
FIG. 8 is a plot showing water loss in detached leaf portions of 34-day-old null segregants (null) and SnRK2-6 transgenic lines of corn plants (transgenic). Each of the data points represents the average of 8 independent transgenic lines of corn plants. Five null segregants and five kinase-containing plants from each independent line, all of which showed very similar size, were used. For each plant, the uppermost leaf with a visible collar was excised and used in the assay. The water loss is reported as a percent of initial fresh weight from 0 minutes to 180 minutes after detachment of the aerial portions from the plant. The significant difference in water loss between null and transgenic lines is illustrated by P (ttest) <0.003.
Figure 9A:
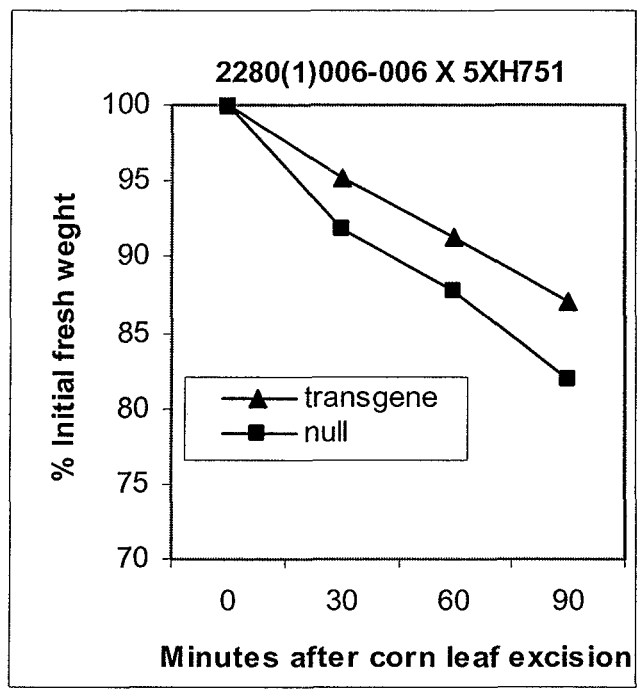
FIGS. 9A-9C are plots showing water loss in detached leaves of 34-day-old null segregants (null) and SnRK2-6-containing corn plants (transgenic) from three independent lines. Each of the data points represents the average of five independent corn plants from the same line. For each plant, the uppermost leaf with a visible collar was excised and used in the assay. The water loss is reported as a percent of initial fresh weight from 0 minutes to 90 minutes after detachment of the aerial portions from the plant.
Figure 9B:
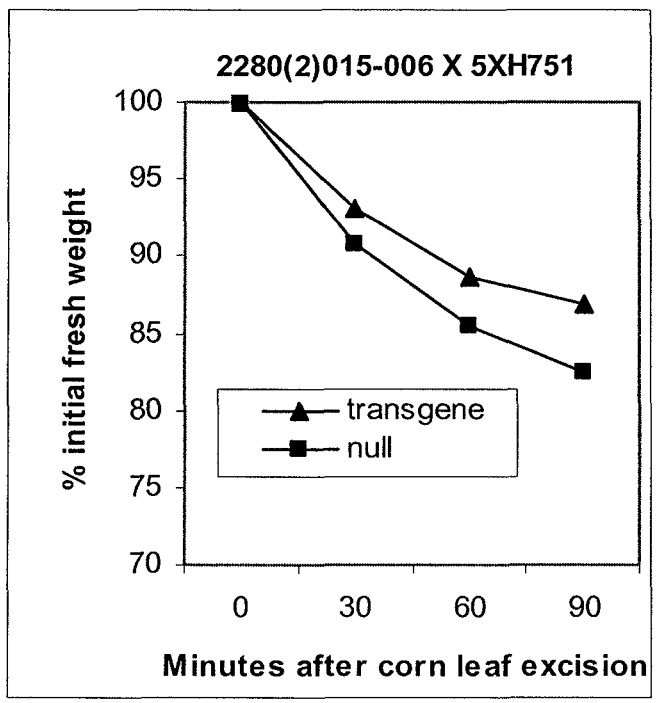
Figure 9C:
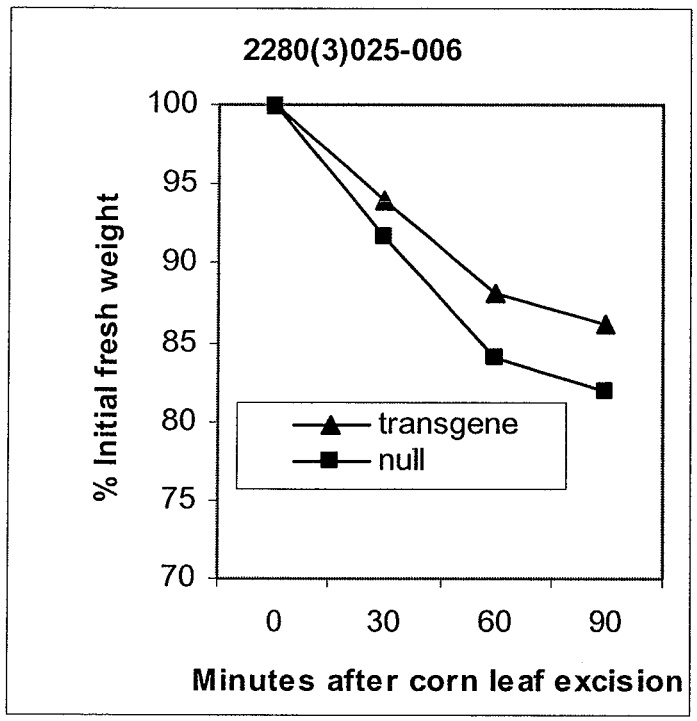

To eradicate the effect resulting from the genomic background difference, eight independent transgenic lines were used to assess the role of the transgene in drought tolerance in corn. In a relation to transpiration rate, water loss in detached leaves of null segregants and SnRK2-6 transgenic plants was measured during a period of leaf detachment. As shown in FIGS. 8 and 9, the transgenic plants showed a reduced rate of water loss compared to null segregants.

The transgenic corn plants appeared more tolerant to drought stress by visual observation. When 30-day-old corn plants were deprived of irrigation for six days, null segregants became more severe wilting than transgenic plants. In addition, transgenic plants were rehydrated much faster than null segregants. In an agreement with this, the biomass of upper parts of transgenic 64-day-old corn plants was 112% to 150% of null segregants at eight days after rehydration prior to which the plants were deprived of irrigation for nine days, as shown in Table 6. In Table 6, biomass of the transgenic plants is expressed as percentage of null segregants which are defined as 100.

TABLE 6

SnRK2-6 transgenic corn plants show a higher recovery rate from dehydration than null segregants.

| Independent T1 line | Parents | | | Biomass (%) of T1 segregants | |
|---|---|---|---|---|---|
| | Female | Transgene(s) in female | Male | Transgenic plants | Null segregants |
| 1 | 2221[1]-003.002 | AAD1 | 5XH751 | 106.3 | 100 |
| 2 | 2221[2]-005.004 | AAD1 | 5XH751 | 80.0 | 100 |
| 3 | 2280[2]-010.005 | AAD1 | 5XH751 | 100.0 | 100 |
| 4 | 2280[1]-002.002 | AAD1 + SnRK2-6 | 5XH751 | 126.3 | 100 |
| 5 | 2280[1]-004.008 | AAD1 + SnRK2-6 | 5XH751 | 127.5 | 100 |
| 6 | 2280[1]-006.006 | AAD1 + SnRK2-6 | 5XH751 | 138.5 | 100 |
| 7 | 2280[1]-008.004 | AAD1 + SnRK2-6 | 5XH751 | 122.2 | 100 |
| 8 | 2280[2]-015.006 | AAD1 + SnRK2-6 | 5XH751 | 152.9 | 100 |
| 9 | 2280[2]-016.004 | AAD1 + SnRK2-6 | 5XH751 | 145.7 | 100 |
| 10 | 2280[3]-023.002 | AAD1 + SnRK2-6 | 5XH751 | 138.4 | 100 |
| 11 | 2280[3]-025.006 | AAD1 + SnRK2-6 | 5XH751 | 112.5 | 100 |
| 12 | 2280[3]-026.005 | AAD1 + SnRK2-6 | 5XH751 | 116.7 | 100 |

In a field experiment conducted in Halfway, Tex., three independent transgenic corn events showed increased grain yield under a drought condition in the grain-filling stage as well as under a well-watered condition compared to their siblings without the SnRK2-6 transgene (null) (Table 7).

TABLE 7

Effect of SnRK2-6 transgene on corn grain yield under different water conditions in the field.

| Event | Transgene | Plot | Location | Relative increase of grain weight per 10 plants (%) | |
|---|---|---|---|---|---|
| | | | | Well watered | Drought stress in the grain filling stage |
| 2280[1]-002.R002.024R. | SnRK2-6 | 101 | Halfway, TX | 16.4 | 11.8 |
| | Null | 102 | Halfway, TX | 0.0 | 0.0 |
| 2280[2]-015.R001.025R. | SnRK2-6 | 103 | Halfway, TX | 29.0 | 33.5 |
| | Null | 104 | Halfway, TX | 0.0 | 0.0 |
| 2280[2]-016.R004.025R. | SnRK2-6 | 105 | Halfway, TX | 14.3 | 8.3 |
| | Null | 106 | Halfway, TX | 0.0 | 0.0 |

Collectively, the above results demonstrate that the constitutive expression of SnRK2-6 can increase corn drought tolerance. This can largely protect corn plants against drought, thereby reducing yield loss under drought condition.

Example 16

Stress Tolerance Genes

SnRK2-6 may be introduced into a plant in combination with one or more genes that confer stress tolerance in plants. Examples of suitable stress tolerance genes are shown in Table 8.

TABLE 8

Genes Involved in Post-Transcriptional Regulations Conferring Increased Abiotic Stress Tolerance

| Gene name | Gene function | Modification | Transgenic phenotype |
|---|---|---|---|
| AtSRL1[a] | Serine-arginine (SR) RNA binding protein | Up-regulation | Salt tolerance |

TABLE 8-continued

Genes Involved in Post-Transcriptional Regulations Conferring Increased Abiotic Stress Tolerance

| Gene name | Gene function | Modification | Transgenic phenotype |
|---|---|---|---|
| GRP2[b] | Glycine Rich RNA binding protein | Up-regulation | Cold and freezing tolerance |
| AtRZ-1a[c] | Glycine Rich RNA binding protein | Up-regulation | Freezing tolerance |
| STRS1, STRS2[d] | DEAD RNA helicase | Loss of function mutant | Tolerance to salt, osmotic, and heat stresses |
| CSD2[e] | Cu/Zn Superoxide Dismutase | Mutagenesis of a miRNA recognition site | Tolerance to oxidative stress conditions (high light, heavy metal, and methyl viologen) |
| XERICO[f] | E3 Ubiquitin ligase | Up-regulation | Drought tolerance by increased ABA level (up-regulation of AtNCED3) |
| HOS1[g] | E3 Ubiquitin ligase | Loss of function mutant | Constitutively vernalized (enhanced cold-responsive gene expression) |

[a]J. Forment, M. A. Naranjo, M. Roldan, R. Serrano and O. Vicente, Expression of *Arabidopsis* SR-like splicing proteins confers salt tolerance to yeast and transgenic plants, *Plant J.* 30 (2002), pp. 511-519.
[b]J. Y. Kim, S. J. Park, B. Jang, C. H. Jung, S. J. Ahn, C. H. Goh, K. Cho, O. Han and H. Kang, Functional characterization of a glycine-rich RNA-binding protein 2 in *Arabidopsis thaliana* under abiotic stress conditions, *Plant J.* 50 (2007), pp. 439-451
[c]Y. O. Kim, J. S. Kim and H. Kang, Cold-inducible zinc finger-containing glycine-rich RNA-binding protein contributes to the enhancement of freezing tolerance in *Arabidopsis thaliana*, *Plant J.* 42 (2005), pp. 890-900.
[d]P. Kant, S. Kant, M. Gordon, R. Shaked and S. Barak, STRESS RESPONSE SUPPRESSOR1 and STRESS RESPONSE SUPPRESSOR2, two DEAD-Box RNA helicases that attenuate *Arabidopsis* responses to multiple abiotic stresses, *Plant Physiol.* 145 (2007), pp. 814-830.
[e]R. Sunkar, A. Kapoor and J.-K. Zhu, Posttranscriptional induction of two Cu/Zn superoxide dismutase genes in *Arabidopsis* is mediated by downregulation of miR398 and important for oxidative stress tolerance, *Plant Cell* 18 (2006), pp. 2051-2065.
[f]J. H. Ko, S. H. Yang and K. H. Han, Upregulation of an *Arabidopsis* RING-H2 gene, XERICO, confers drought tolerance through increased abscisic acid biosynthesis, *Plant J.* 47 (2006), pp. 343-355.
[g]C. H. Dong, M. Agarwal, Y. Zhang, Q. Xie and J. K. Zhu, The negative regulator of plant cold responses, HOS1, is a RING E3 ligase that mediates the ubiquitination and degradation of ICE1, *Proc. Natl. Acad. Sci. U.S.A.* 103 (2006), pp. 8281-8286.

Example 17

Drought Tolerance Genes

SnRK2-6 may be introduced into a plant in combination with one or more genes that confer drought tolerance in plants. Examples of suitable drought tolerance genes are shown in Table 9.

TABLE 9

Drought Tolerance Genes

| Genes | Function | Mechanism of action | References |
|---|---|---|---|
| DREBs/CBFs; ABF3 | Stress induced transcription factors | Enhanced expression of downstream stress related genes confers drought/cold/salt tolerance. Constitutively overexpression can lead to stunting growth | Oh et al. (2005), Ito et al. (2006) |
| SNAC1 | Stress induced transcription factor | SNAC1 expression reduces water loss increasing stomatal sensitivity to ABA | Hu et al. (2006) |
| OsCDPK7 | Stress induced Ca-dependent protein kinase | Enhanced expression of stress responsive genes | Saijo et al. (2000) |
| Farnesyl-transferase (ERA1) | Negative-regulator of ABA sensing | Down-regulation of farnesyltransferase enhances the plant's response to ABA and drought tolerance reducing stomatal conductance | Wang et al. (2005) |
| Mn-SOD | Mn-superoxide dismutase | Overexpression improves stress tolerance also in field conditions | McKersie et al. (1996) |
| AVP1 | Vacuolar H$^+$-pyrophosphatase | Overexpression facilitate auxin fluxes leading to increased root growth | Gaxiola et al. (2001), Park et al. (2005) |
| HVA1; OsLEA3 | Stress induced LEA proteins | Over-accumulation of LEA increases drought tolerance also in field conditions | Bahieldin et al. (2005), Xiao et al. (2007) |

TABLE 9-continued

Drought Tolerance Genes

| Genes | Function | Mechanism of action | References |
|---|---|---|---|
| ERECTA | A putative leucine-rich repeat receptor-like kinase is a major contributor to a locus for Δ on *Arabidopsis* chromosome 2 | ERECTA acts as a regulator of transpiration efficiency with effects on stomatal density, epidermal cell expansion, mesophyll cell proliferation and cell-cell contact | Masle et al. (2005) |
| otsA and otsB | *Escherichia coli* trehalose biosynthetic genes | Increased trehalose accumulation correlates with higher soluble carbohydrate levels, elevated photosynthetic capacity and increased tolerance to photo-oxidative damage | Garg et al. (2002) |
| P5CS | δ-Pyrroline-5-carboxylate synthetase | Enhanced accumulation of proline leads to increased osmotolerance | Kavi Kishor et al. (1995), Zhu et al. (1998) |
| mtlD | Mannitol-1-phosphate dehydrogenase | Mannitol accumulation leads to increased osmotolerance | Abebe et al. (2003) |
| GF14λ | 14-3-3 protein | Lines overexpressing GF14λ have a "stay green" phenotype, improved water stress tolerance and higher photosynthetic rates under water deficit conditions | Yan et al. (2004) |
| NADP-Me | NADP-malic enzyme | The overexpression decreased stomatal conductance and improves WUE | Laporte et al. (2002) |

While this invention has been described in certain example embodiments, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

All references, including publications, patents, and patent applications, cited herein are hereby incorporated by reference to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

What is claimed is:

1. A process for producing a plant, plant seed or progeny thereof, the process comprising:
transforming a plant cell with a heterologous nucleic acid sequence encoding a Snf1-related protein kinase 2-6 protein; wherein the heterologous nucleic acid comprises SEQ ID NO:4;
growing a plant from the plant cell until the plant produces seed;
and harvesting the seed from the plant; wherein the plant is selected from the group consisting of consisting of *Arabidopsis thaliana, Borago* spp., Canola, *Ricinus* spp., *Theobroma* spp., *Zea* spp., *Gossypium* spp., *Crambe* spp., *Cuphea* spp., *Linum* spp., *Lesquerella* spp., *Limnanthes* spp., Linola, *Tropaeolum* spp., *Oenothera* spp., *Olea* spp., *Elaeis* spp., *Arachis* spp., rapeseed, *Cartha-mus* spp., *Glycine* spp., *Soja* spp., *Helianthus* spp., *Nicotiana* spp., *Vernonia* spp., *Triticum* spp., *Hordeum* spp., *Oryza* spp., *Avena* spp., *Sorghum* spp., *Secale* spp., Brassicaceae, and other members of the plant family Gramineae; and wherein the plant, plant storage organ or plant seed displays enhanced phenotypic traits.

2. The process of claim 1, wherein the nucleic acid sequence encoding the Snf1-related protein kinase 2-6 protein is integrated into a genome of the plant cell.

3. The process of claim 1, further comprising selecting the seed having the nucleic acid sequence encoding the Snf1-related protein kinase 2-6 protein integrated into a genome of the plant cell.

4. A seed comprising the heterologous nucleic acid sequence encoding a Snf1-related protein kinase 2-6 protein harvested from the plant produced by the process of claim 1.

5. The process of claim 1, further comprising:
planting the seed in soil;
growing a second plant from the seed; and
harvesting the seed from the second plant.

6. The process of claim 1, wherein transforming the plant cell with the nucleic acid sequence encoding the Snf1-related protein kinase 2-6 protein comprises:
transforming an *Agrobacterium* cell with the nucleic acid sequence encoding the Snf1-related protein kinase 2-6 protein; and
transforming the plant cell with the *Agrobacterium* cell.

7. The process of claim 3, wherein selecting the seed having the nucleic acid sequence encoding the Snf1-related protein kinase 2-6 protein integrated into the genome of the plant cell comprises:
isolating genomic nucleic acid from the seed; and
amplifying the nucleic acid sequence encoding the Snf1-related protein kinase 2-6 protein from the isolated genomic nucleic acid from the seed.

8. The process according to claim 1, further comprising extracting oil from the harvested seed.

9. A plant, plant seed, or progeny thereof having a heterologous nucleic acid sequence encoding a Snf1-related protein kinase 2-6 protein incorporated in a genome thereof; wherein the heterologous nucleic acid comprises SEQ ID NO:4; and wherein the plant is selected from the group consisting of *Arabidopsis thaliana, Borazo* spp., Canola, *Ricinus* spp., *Theobroma* spp., *Zea* spp., *Gossypium* spp., *Crambe* spp., *Cuphea* spp., *Linum* spp., *Lesquerella* spp., *Limnanthes* spp., Linola, *Tropaeolum* spp., *Oenothera* spp., *Olea* spp., *Elaeis* spp., *Arachis* spp., rapeseed, *Carthamus* spp., *Glycine* spp., *Sofa* spp., *Helianthus* spp., *Nicotiana* spp., *Vernonia* spp., *Triticum* spp., *Hordeum* spp., *Orvza* spp., *Avena* spp., *Sorghum* spp., *Secale* spp., Brassicaceae, and other members of the plant family Gramineae; and wherein the plant, plant storage organ or plant seed displays enhanced phenotypic traits.

10. A method of changing the oil, sugar, or starch content of a plant, plant storage organ or plant seed, said process comprising:
introducing a nucleic acid construct into a plant transformation vector to produce a modified plant transformation vector, wherein said nucleic acid construct comprises a heterologous isolated, purified or recombinant nucleic acid sequence encoding an Arabidopsis Snf1-related protein kinase 2-6 (SnRK2-6) protein; wherein the heterologous isolated, purified or recombinant nucleic acid comprises SEQ ID NO:4;
transforming said plant, plant storage organ or plant seed's genome with said modified plant transformation vector; and growing said plant, plant storage organ or plant seed and extracting said oil, sugar, or starch; wherein the plant is selected from the group consisting of consisting of *Arabidopsis thaliana, Borago* spp., Canola, *Ricinus* spp., *Theobroma* spp., *Zea* spp., *Gossypium* spp., *Crambe* spp., *Cuphea* spp., *Linum* spp., *Lesquerella* spp., *Limnanthes* spp., Linola, *Tropaeolum* spp., *Oenothera* spp., *Olea* spp., *Elaeis* spp., *Arachis* spp., rapeseed, *Carthamus* spp., *Glycine* spp., *Soja* spp., *Helianthus* spp., *Nicotiana* spp., *Vernonia* spp., *Triticum* spp., *Hordeum* spp., *Oryza* spp., *Avena* spp., *Sorghum* spp., *Secale* spp., Brassicaceae, and other members of the plant family Gramineae; and wherein the plant, plant storage organ or plant seed displays enhanced phenotypic traits.

11. A genetically transformed plant, produced by the method of claim 10.

12. A genetically transformed plant seed, produced by the method of claim 10.

13. The genetically transformed plant of claim 11, wherein the enhanced phenotypic traits is an altered respiration rate as compared to a genomically unmodified plant of the same genotype.

14. The genetically transformed plant of claim 11, wherein the enhanced phenotypic traits is an altered seed oil content as compared to a genomically unmodified plant of the same genotype.

15. The genetically transformed plant of claim 11, wherein the enhanced phenotypic traits is an altered fatty acid composition as compared to a genomically unmodified plant of the same genotype.

16. The genetically transformed plant of claim 11, wherein the enhanced phenotypic traits is an enhanced biomass as compared to a genomically unmodified plant of the same genotype.

17. The genetically transformed plant of claim 11, wherein the enhanced phenotypic traits is an enhanced capacity to accumulate biopolymers as compared to a genomically unmodified plant of the same genotype.

18. The genetically transformed plant of claim 11, wherein the enhanced phenotypic traits is an altered carbohydrate content as compared to a genomically unmodified plant of the same genotype.

19. The genetically transformed plant of claim 18, wherein the enhanced phenotypic traits is an altered sucrose and starch content as compared to a genomically unmodified plant of the same genotype.

20. The genetically transformed plant seed of claim 12, wherein the enhanced phenotypic traits is an altered respiration rate as compared to a genomically unmodified plant of the same genotype.

21. The genetically transformed plant seed of claim 12, wherein the enhanced phenotypic traits is an altered seed oil content as compared to a genomically unmodified plant of the same genotype.

22. The genetically transformed plant seed of claim 12, wherein the seed produces a plant which exhibits an enhanced fatty acid composition compared to a genomically unmodified plant of the same genotype.

23. The genetically transformed plant seed of claim 12, wherein the seed produces a plant which exhibits an enhanced biomass compared to a genomically unmodified plant of the same genotype.

24. The genetically transformed plant seed of claim 12, wherein the seed produces a plant which exhibits an enhanced capacity to accumulate biopolymers compared to a genomically unmodified plant of the same genotype.

25. A method of modulating the level of Snf1-related protein kinase 2-6 protein in a plant, comprising: stably transforming a plant cell with a heterologous plant Snf1-related protein kinase polynucleotide operably linked to a promoter; wherein the heterologous plant Snf1-related protein kinase polynucleotide comprises SEQ ID NO:4;
and growing the plant cell under plant growing conditions to produce a regenerated plant capable of expressing the polynucleotide for a time sufficient to modulate the Snf1-related protein kinase 2-6 protein levels in the plant; wherein the plant cell is selected from the group consisting of *Arabidopsis thaliana, Borago* spp., Canola, *Ricinus* spp., *Theobroma* spp., *Zea* spp., *Gossypium* spp., *Crambe* spp., *Cuphea* spp., *Linum* spp., *Lesquerella* spp., *Limnanthes* spp., Linola, *Tropaeolum* spp., *Oenothera* spp., *Olea* spp., *Elaeis* spp., *Arachis* spp., rapeseed, *Carthamus*spp., *Glycine* spp., *Soja* spp., Helianthus spp., Nicotiana spp., Vernonia spp., Triticum spp., Hordeum spp., Oryza spp., Avena spp., Sorghum spp., Secale spp., Brassicaceae, and other members of the plant family Gramineae, and wherein the plant, plant storage organ or plant seed displays enhanced phenotypic traits.

26. A process for extracting oil from a transgenic seed, the process comprising:
   transforming a plant cell with means for encoding a Snf1-related protein kinase 2-6 protein;
   wherein the Snf1-related protein kinase 2-6 protein is encoded on a heterologous polynucleotide selected from the group consisting o SEQ ID NO:4;
   growing a plant from the plant cell until the plant produces seed;
   harvesting the seed from the plant; and
   extracting oil from the harvested seed;
   wherein the plant cell is selected from the group consisting of Borago spp., Canola, Ricinus spp., Theobroma spp., Zea spp., Gossypium spp, Crambe spp., Cuphea spp., Linum spp., Lesquerella spp., Limnanthes spp., Linola, Tropaeolum spp., Oenothera spp., Olea spp., Elaeis spp., Arachis spp., rapeseed, Carthamus spp., Glycine spp., Soja spp., Helianthus spp., Nicotiana spp., Vernonia spp., Triticum spp., Hordeum spp., Oryza spp., Avena spp., Sorghum spp., Secale spp., Brassicaceae, and other members of the plant family Gramineae; and
   wherein the plant, plant storage organ or plant seed displays enhanced phenotypic traits.

27. A method of changing the oil content, fatty acid composition, sugar/starch/carbohydrate levels or seed yield of a plant by introducing a nucleic acid construct into a plant transformation vector,
   using the vector to transform the genome of a plant or plant seed,
   and then growing the plant or plant seed and extracting the oil from the plant seed, characterized in that said nucleic construct comprises SEQ ID NO:4, and wherein the nucleic acid construct is heterologous to the plant; and wherein the plant is selected from the group consisting of Arabidopsis thaliana, Borago spp., Canola, Ricinus spp., Theobroma spp., Zea spp., Gossypium spp, Crambe spp, Cuphea spp., Linum spp., Lesquerella spp., Limnanthes spp., Linola, Tropaeolum spp., Oenothera spp., Olea spp., Elaeis spp., Arachis spp., rapeseed, Carthamus spp., Glycine spp., Soja spp., Helianthus spp., Nicotiana spp., Vernonia spp., Triticum spp., Hordeum spp., Oryza spp., Avena spp., Sorghum spp., Secale spp., Brassicaceae, and other members of the plant family Gramineae.

28. A method of altering the drought tolerance of a plant, said method comprising:
   introducing a nucleic acid construct comprising a heterologous nucleic acid sequence comprising SEQ ID NO:4, encoding a polypeptide having Snf1 related protein kinase 2-6 activity into a plant transformation vector;
   transforming the genome of a plant or plant seed with said plant transformation vector; expressing the nucleic acid sequence;
   growing the plant or plant seed;
   and selecting a transformed plant having the altered drought tolerance as compared to an average drought tolerance of a statistically significant number of plants of the same genotype as the plant grown in identical conditions, but without the introduced nucleotide sequence.

29. A method of altering the root biomass of a plant, said method comprising:
   introducing a nucleic acid construct comprising a heterologous nucleic acid sequence comprising SEQ ID NO:4, encoding a polypeptide having Snf-1 related protein kinase 2-6 activity into a plant transformation vector;
   transforming the genome of a plant or plant seed with said plant transformation vector; expressing the nucleic acid sequence;
   growing the plant or plant seed;
   and selecting a transformed plant having the altered root biomass as compared to an average root biomass of a statistically significant number of plants of the same genotype as the plant grown in identical conditions, but without the introduced nucleotide sequence; wherein the plant or plant seed is selected from the group consisting of consisting of Arabidopsis thaliana, Borago spp., Canola, Ricinus spp., Theobroma spp., Zea spp., Gossypium spp., Crambe spp., Cuphea spp., Linum spp., Lesquerella spp., Limnanthes spp., Linola, Tropaeolum spp., Oenothera spp., Olea spp., Elaeis spp., Arachis spp., rapeseed, Carthamus spp., Glycine spp., Soja spp., Helianthus spp., Nicotiana spp., Vernonia spp., Triticum spp., Hordeum spp., Oryra spp., Avena spp., Sorghum spp., Secale spp., Brassicaceae, and other members of the plant family Gramineae.

30. The plant, plant seed, or progeny thereof of claim 9, comprising one or more additional heterologous nucleic acid sequences which impart enhanced resistance to water loss, drought tolerance, carbon assimilation, plant growth and development, fatty acid bioassembly, or root growth in the plant, plant seed, or progeny.

31. The method according to claim 10, wherein the nucleic acid construct is a sense nucleic acid construct.

32. The method according to claim 25, wherein the polynucleotide is in the sense orientation.

33. The method according to claim 27, wherein the nucleic acid construct is a sense nucleic acid construct.

34. A process for producing a plant, plant seed or progeny thereof, the process comprising:
   transforming a plant cell with a heterologous nucleic acid sequence encoding a Snf1-related protein kinase 2-6 protein;
   growing a plant from the plant cell until the plant produces seed; and
   harvesting the seed from the plant;
   wherein the nucleic acid sequence encoding a Snf1-related protein kinase 2-6 protein comprises SEQ ID NO:4.

* * * * *

SEQUENCE LISTING

```
<160> NUMBER OF SEQ ID NOS: 44

<210> SEQ ID NO 1
<211> LENGTH: 1089
<212> TYPE: DNA
<213> ORGANISM: Arabidopsis thaliana
<220> FEATURE:
<221> NAME/KEY: CDS
<222> LOCATION: (1)..(1089)

<400> SEQUENCE: 1 atg gat cga cca gca gtg agt ggt cca atg gat ttg ccg att atg cac      48
Met Asp Arg Pro Ala Val Ser Gly Pro Met Asp Leu Pro Ile Met His
1               5                   10                  15 gat agt gat agg tat gaa ctc gtc aag gat att ggc tcc ggt aat ttt      96
Asp Ser Asp Arg Tyr Glu Leu Val Lys Asp Ile Gly Ser Gly Asn Phe
                20                  25                  30 gga gtt gcg aga ttg atg aga gac aag caa agt aat gag ctt gtt gct     144
Gly Val Ala Arg Leu Met Arg Asp Lys Gln Ser Asn Glu Leu Val Ala
            35                  40                  45 gtt aaa tat atc gag aga ggt gag aag ata gat gaa aat gta aaa agg     192
Val Lys Tyr Ile Glu Arg Gly Glu Lys Ile Asp Glu Asn Val Lys Arg
        50                  55                  60
```

-continued

```
gag ata atc aac cac agg tcc tta aga cat ccc aat atc gtt aga ttc      240
Glu Ile Ile Asn His Arg Ser Leu Arg His Pro Asn Ile Val Arg Phe
 65              70                  75                  80 aaa gag gtt ata tta aca cca acc cat tta gcc att gtt atg gaa tat      288
Lys Glu Val Ile Leu Thr Pro Thr His Leu Ala Ile Val Met Glu Tyr
                 85                  90                  95 gca tct gga gga gaa ctt ttc gag cga atc tgc aat gca ggc cgc ttc      336
Ala Ser Gly Gly Glu Leu Phe Glu Arg Ile Cys Asn Ala Gly Arg Phe
            100                 105                 110 agc gaa gac gag gcg agg ttt ttc ttc cag caa ctc att tca gga gtt      384
Ser Glu Asp Glu Ala Arg Phe Phe Phe Gln Gln Leu Ile Ser Gly Val
        115                 120                 125 agt tac tgt cat gct atg caa gta tgt cac cga gac tta aag ctc gag      432
Ser Tyr Cys His Ala Met Gln Val Cys His Arg Asp Leu Lys Leu Glu
    130                 135                 140 aat acg tta tta gat ggt agc ccg gcc cct cgt cta aag ata tgt gat      480
Asn Thr Leu Leu Asp Gly Ser Pro Ala Pro Arg Leu Lys Ile Cys Asp
145                 150                 155                 160 ttc gga tat tct aag tca tca gtg tta cat tcg caa cca aaa tca act      528
Phe Gly Tyr Ser Lys Ser Ser Val Leu His Ser Gln Pro Lys Ser Thr
                165                 170                 175 gtt gga act cct gct tac atc gct cct gag gtt tta cta aag aaa gaa      576
Val Gly Thr Pro Ala Tyr Ile Ala Pro Glu Val Leu Leu Lys Lys Glu
            180                 185                 190 tat gat gga aag gtt gca gat gtt tgg tct tgt ggg gtt act ctg tat      624
Tyr Asp Gly Lys Val Ala Asp Val Trp Ser Cys Gly Val Thr Leu Tyr
        195                 200                 205 gtc atg ctg gtt gga gca tat cct ttc gaa gat ccc gag gaa cca aag      672
Val Met Leu Val Gly Ala Tyr Pro Phe Glu Asp Pro Glu Glu Pro Lys
210                 215                 220 aat ttc agg aaa act ata cat aga atc ctg aat gtt cag tat gct att      720
Asn Phe Arg Lys Thr Ile His Arg Ile Leu Asn Val Gln Tyr Ala Ile
225                 230                 235                 240 ccg gat tat gtt cac ata tct cct gaa tgt cgc cat ttg atc tcc aga      768
Pro Asp Tyr Val His Ile Ser Pro Glu Cys Arg His Leu Ile Ser Arg
                245                 250                 255 ata ttt gtt gct gac cct gca aag agg ata tca att cct gaa ata agg      816
Ile Phe Val Ala Asp Pro Ala Lys Arg Ile Ser Ile Pro Glu Ile Arg
            260                 265                 270 aac cat gaa tgg ttt cta aag aat cta ccg gca gat cta atg aac gat      864
Asn His Glu Trp Phe Leu Lys Asn Leu Pro Ala Asp Leu Met Asn Asp
        275                 280                 285 aac acg atg acc act cag ttt gat gaa tcg gat caa ccg ggc caa agc      912
Asn Thr Met Thr Thr Gln Phe Asp Glu Ser Asp Gln Pro Gly Gln Ser
    290                 295                 300 ata gaa gaa att atg cag atc att gca gaa gca act gtt cct cct gca      960
Ile Glu Glu Ile Met Gln Ile Ile Ala Glu Ala Thr Val Pro Pro Ala
305                 310                 315                 320 ggc act cag aat ctg aac cat tac ctc aca gga agc ttg gac ata gat     1008
Gly Thr Gln Asn Leu Asn His Tyr Leu Thr Gly Ser Leu Asp Ile Asp
                325                 330                 335 gac gat atg gag gaa gac tta gag agc gac ctt gat gat ctt gac atc     1056
Asp Asp Met Glu Glu Asp Leu Glu Ser Asp Leu Asp Asp Leu Asp Ile
            340                 345                 350 gac agt agc gga gag att gtg tac gca atg tga                         1089
Asp Ser Ser Gly Glu Ile Val Tyr Ala Met
        355                 360
```

```
<210> SEQ ID NO 2
<211> LENGTH: 362
<212> TYPE: PRT
<213> ORGANISM: Arabidopsis thaliana

<400> SEQUENCE: 2
```

| | | | | | | | | | | | | | | |
|---|---|---|---|---|---|---|---|---|---|---|---|---|---|---|
| Met | Asp | Arg | Pro | Ala | Val | Ser | Gly | Pro | Met | Asp | Leu | Pro | Ile | Met | His |
| 1 | | | | 5 | | | | | 10 | | | | | 15 | |

| Asp | Ser | Asp | Arg | Tyr | Glu | Leu | Val | Lys | Asp | Ile | Gly | Ser | Gly | Asn | Phe |
|---|---|---|---|---|---|---|---|---|---|---|---|---|---|---|---|
| | | | 20 | | | | | 25 | | | | | 30 | | |

| Gly | Val | Ala | Arg | Leu | Met | Arg | Asp | Lys | Gln | Ser | Asn | Glu | Leu | Val | Ala |
| | | 35 | | | | | 40 | | | | | 45 | | | |

| Val | Lys | Tyr | Ile | Glu | Arg | Gly | Glu | Lys | Ile | Asp | Glu | Asn | Val | Lys | Arg |
| 50 | | | | | 55 | | | | | 60 | | | | | |

| Glu | Ile | Ile | Asn | His | Arg | Ser | Leu | Arg | His | Pro | Asn | Ile | Val | Arg | Phe |
| 65 | | | | | 70 | | | | | 75 | | | | | 80 |

| Lys | Glu | Val | Ile | Leu | Thr | Pro | Thr | His | Leu | Ala | Ile | Val | Met | Glu | Tyr |
| | | | | 85 | | | | | 90 | | | | | 95 | |

| Ala | Ser | Gly | Gly | Glu | Leu | Phe | Glu | Arg | Ile | Cys | Asn | Ala | Gly | Arg | Phe |
| | | | 100 | | | | | 105 | | | | | 110 | | |

| Ser | Glu | Asp | Glu | Ala | Arg | Phe | Phe | Gln | Gln | Leu | Ile | Ser | Gly | Val |
| | | 115 | | | | | 120 | | | | | 125 | | | |

| Ser | Tyr | Cys | His | Ala | Met | Gln | Val | Cys | His | Arg | Asp | Leu | Lys | Leu | Glu |
| | | 130 | | | | | 135 | | | | | 140 | | | |

| Asn | Thr | Leu | Leu | Asp | Gly | Ser | Pro | Ala | Pro | Arg | Leu | Lys | Ile | Cys | Asp |
| 145 | | | | | 150 | | | | | 155 | | | | | 160 |

| Phe | Gly | Tyr | Ser | Lys | Ser | Ser | Val | Leu | His | Ser | Gln | Pro | Lys | Ser | Thr |
| | | | | 165 | | | | | 170 | | | | | 175 | |

| Val | Gly | Thr | Pro | Ala | Tyr | Ile | Ala | Pro | Glu | Val | Leu | Leu | Lys | Lys | Glu |
| | | | 180 | | | | | 185 | | | | | 190 | | |

| Tyr | Asp | Gly | Lys | Val | Ala | Asp | Val | Trp | Ser | Cys | Gly | Val | Thr | Leu | Tyr |
| | | | 195 | | | | | 200 | | | | | 205 | | |

| Val | Met | Leu | Val | Gly | Ala | Tyr | Pro | Phe | Glu | Asp | Pro | Glu | Glu | Pro | Lys |
| | 210 | | | | | 215 | | | | | 220 | | | | |

| Asn | Phe | Arg | Lys | Thr | Ile | His | Arg | Ile | Leu | Asn | Val | Gln | Tyr | Ala | Ile |
| 225 | | | | | 230 | | | | | 235 | | | | | 240 |

| Pro | Asp | Tyr | Val | His | Ile | Ser | Pro | Glu | Cys | Arg | His | Leu | Ile | Ser | Arg |
| | | | | 245 | | | | | 250 | | | | | 255 | |

| Ile | Phe | Val | Ala | Asp | Pro | Ala | Lys | Arg | Ile | Ser | Ile | Pro | Glu | Ile | Arg |
| | | | 260 | | | | | 265 | | | | | 270 | | |

| Asn | His | Glu | Trp | Phe | Leu | Lys | Asn | Leu | Pro | Ala | Asp | Leu | Met | Asn | Asp |
| | | 275 | | | | | 280 | | | | | 285 | | | |

| Asn | Thr | Met | Thr | Thr | Gln | Phe | Asp | Glu | Ser | Asp | Gln | Pro | Gly | Gln | Ser |
| | 290 | | | | | 295 | | | | | 300 | | | | |

| Ile | Glu | Glu | Ile | Met | Gln | Ile | Ile | Ala | Glu | Ala | Thr | Val | Pro | Pro | Ala |
| 305 | | | | | 310 | | | | | 315 | | | | | 320 |

| Gly | Thr | Gln | Asn | Leu | Asn | His | Tyr | Leu | Thr | Gly | Ser | Leu | Asp | Ile | Asp |
| | | | | 325 | | | | | 330 | | | | | 335 | |

| Asp | Asp | Met | Glu | Glu | Asp | Leu | Glu | Ser | Asp | Leu | Asp | Asp | Leu | Asp | Ile |
| | | | 340 | | | | | 345 | | | | | 350 | | |

| Asp | Ser | Ser | Gly | Glu | Ile | Val | Tyr | Ala | Met |
| | | | 355 | | | | | 360 | |

```
<210> SEQ ID NO 3
<211> LENGTH: 1089
<212> TYPE: DNA
<213> ORGANISM: Artificial Sequence
<220> FEATURE:
<223> OTHER INFORMATION: Synthetic Construct - Plant-Optimized DNA
      SnRK2-6 hv5
<220> FEATURE:
<221> NAME/KEY: CDS
<222> LOCATION: (1)..(1089)

<400> SEQUENCE: 3
```

| | | | | | | | | | | | | | | | | |
|---|---|---|---|---|---|---|---|---|---|---|---|---|---|---|---|---|
| atg | gat | cgc | cca | gct | gtt | tcc | ggt | cca | atg | gac | ttg | ccc | atc | atg | cat | 48 |
| Met | Asp | Arg | Pro | Ala | Val | Ser | Gly | Pro | Met | Asp | Leu | Pro | Ile | Met | His | |
| 1 | | | | 5 | | | | | 10 | | | | | 15 | | |
| gac | tct | gac | aga | tat | gaa | ctt | gtc | aag | gac | att | ggc | tcc | ggc | aac | ttt | 96 |
| Asp | Ser | Asp | Arg | Tyr | Glu | Leu | Val | Lys | Asp | Ile | Gly | Ser | Gly | Asn | Phe | |
| | | | 20 | | | | | 25 | | | | | 30 | | | |
| ggt | gtt | gcc | aga | ttg | atg | agg | gac | aag | caa | agc | aac | gag | ctt | gtt | gct | 144 |
| Gly | Val | Ala | Arg | Leu | Met | Arg | Asp | Lys | Gln | Ser | Asn | Glu | Leu | Val | Ala | |
| | 35 | | | | | 40 | | | | | 45 | | | | | |
| gtc | aag | tac | att | gag | agg | ggt | gag | aag | ata | gat | gag | aat | gtg | aaa | cgt | 192 |
| Val | Lys | Tyr | Ile | Glu | Arg | Gly | Glu | Lys | Ile | Asp | Glu | Asn | Val | Lys | Arg | |
| 50 | | | | | 55 | | | | | 60 | | | | | | |
| gag | atc | atc | aac | cac | cgc | tcc | ctc | cgt | cat | ccc | aac | ata | gtg | cgc | ttc | 240 |
| Glu | Ile | Ile | Asn | His | Arg | Ser | Leu | Arg | His | Pro | Asn | Ile | Val | Arg | Phe | |
| 65 | | | | 70 | | | | | 75 | | | | | 80 | | |
| aaa | gag | gtc | atc | ctc | act | ccc | acc | cac | ctc | gcc | att | gtc | atg | gag | tat | 288 |
| Lys | Glu | Val | Ile | Leu | Thr | Pro | Thr | His | Leu | Ala | Ile | Val | Met | Glu | Tyr | |
| | | | 85 | | | | | 90 | | | | | 95 | | | |
| gca | tct | ggg | gga | gaa | ctc | ttc | gag | agg | atc | tgc | aat | gct | ggg | agg | ttc | 336 |
| Ala | Ser | Gly | Gly | Glu | Leu | Phe | Glu | Arg | Ile | Cys | Asn | Ala | Gly | Arg | Phe | |
| | | 100 | | | | | 105 | | | | | 110 | | | | |
| tca | gaa | gat | gag | gca | agg | ttc | ttt | ttc | cag | caa | ctc | atc | tct | gga | gtc | 384 |
| Ser | Glu | Asp | Glu | Ala | Arg | Phe | Phe | Phe | Gln | Gln | Leu | Ile | Ser | Gly | Val | |
| | | | 115 | | | | | 120 | | | | | 125 | | | |
| agc | tac | tgc | cat | gca | atg | caa | gtg | tgc | cac | cgt | gac | ttg | aag | ttg | gaa | 432 |
| Ser | Tyr | Cys | His | Ala | Met | Gln | Val | Cys | His | Arg | Asp | Leu | Lys | Leu | Glu | |
| | 130 | | | | | 135 | | | | | 140 | | | | | |
| aac | aca | ctt | ttg | gat | ggt | tct | cca | gcc | cct | cgt | ctc | aag | atc | tgt | gac | 480 |
| Asn | Thr | Leu | Leu | Asp | Gly | Ser | Pro | Ala | Pro | Arg | Leu | Lys | Ile | Cys | Asp | |
| 145 | | | | | 150 | | | | | 155 | | | | | 160 | |
| ttt | ggc | tac | tcc | aaa | tca | tct | gtg | ctt | cac | tcc | cag | cca | aag | tca | aca | 528 |
| Phe | Gly | Tyr | Ser | Lys | Ser | Ser | Val | Leu | His | Ser | Gln | Pro | Lys | Ser | Thr | |
| | | | 165 | | | | | 170 | | | | | 175 | | | |
| gtg | gga | act | cca | gca | tac | atc | gct | ccc | gag | gtc | ctc | ttg | aag | aaa | gag | 576 |
| Val | Gly | Thr | Pro | Ala | Tyr | Ile | Ala | Pro | Glu | Val | Leu | Leu | Lys | Lys | Glu | |
| | | 180 | | | | | 185 | | | | | 190 | | | | |
| tat | gat | gga | aag | gtg | gct | gat | gtt | tgg | tct | tgt | ggg | gtg | acc | ctc | tat | 624 |
| Tyr | Asp | Gly | Lys | Val | Ala | Asp | Val | Trp | Ser | Cys | Gly | Val | Thr | Leu | Tyr | |
| | | | 195 | | | | | 200 | | | | | 205 | | | |
| gtc | atg | ctt | gtg | gga | gcc | tac | cct | ttt | gaa | gat | cct | gaa | gag | cca | aag | 672 |
| Val | Met | Leu | Val | Gly | Ala | Tyr | Pro | Phe | Glu | Asp | Pro | Glu | Glu | Pro | Lys | |
| | 210 | | | | | 215 | | | | | 220 | | | | | |
| aat | ttc | cgc | aaa | acc | atc | cac | aga | atc | ctt | aat | gtt | caa | tat | gcc | att | 720 |
| Asn | Phe | Arg | Lys | Thr | Ile | His | Arg | Ile | Leu | Asn | Val | Gln | Tyr | Ala | Ile | |
| 225 | | | | | 230 | | | | | 235 | | | | | 240 | |
| cca | gat | tac | gtt | cac | ata | tct | ccc | gaa | tgc | aga | cac | ttg | atc | tcc | aga | 768 |
| Pro | Asp | Tyr | Val | His | Ile | Ser | Pro | Glu | Cys | Arg | His | Leu | Ile | Ser | Arg | |
| | | | 245 | | | | | 250 | | | | | 255 | | | |

```
atc ttt gtt gct gac cca gca aag aga ata tca att cct gag att agg    816
Ile Phe Val Ala Asp Pro Ala Lys Arg Ile Ser Ile Pro Glu Ile Arg
        260                 265                 270 aat cat gaa tgg ttc ttg aag aac ctt cct gcc gac ctc atg aat gac    864
Asn His Glu Trp Phe Leu Lys Asn Leu Pro Ala Asp Leu Met Asn Asp
            275                 280                 285 aac aca atg acc act cag ttc gat gaa tct gat caa cct ggc cag agc    912
Asn Thr Met Thr Thr Gln Phe Asp Glu Ser Asp Gln Pro Gly Gln Ser
    290                 295                 300 ata gag gaa atc atg cag atc att gct gag gca act gtt cct cca gct    960
Ile Glu Glu Ile Met Gln Ile Ile Ala Glu Ala Thr Val Pro Pro Ala
305                 310                 315                 320 ggc aca cag aac ttg aac cat tac ctc acc ggc agc ttg gac att gat   1008
Gly Thr Gln Asn Leu Asn His Tyr Leu Thr Gly Ser Leu Asp Ile Asp
                325                 330                 335 gat gac atg gag gaa gat ctt gag agc gac ctt gat gac ctt gac att   1056
Asp Asp Met Glu Glu Asp Leu Glu Ser Asp Leu Asp Asp Leu Asp Ile
            340                 345                 350 gac tcc agc ggt gag att gtg tac gcc atg tga                        1089
Asp Ser Ser Gly Glu Ile Val Tyr Ala Met
        355                 360

<210> SEQ ID NO 4
<211> LENGTH: 362
<212> TYPE: PRT
<213> ORGANISM: Artificial Sequence
<220> FEATURE:
<223> OTHER INFORMATION: Synthetic Construct

<400> SEQUENCE: 4

Met Asp Arg Pro Ala Val Ser Gly Pro Met Asp Leu Pro Ile Met His
1               5                   10                  15

Asp Ser Asp Arg Tyr Glu Leu Val Lys Asp Ile Gly Ser Gly Asn Phe
            20                  25                  30

Gly Val Ala Arg Leu Met Arg Asp Lys Gln Ser Asn Glu Leu Val Ala
        35                  40                  45

Val Lys Tyr Ile Glu Arg Gly Glu Lys Ile Asp Glu Asn Val Lys Arg
    50                  55                  60

Glu Ile Ile Asn His Arg Ser Leu Arg His Pro Asn Ile Val Arg Phe
65                  70                  75                  80

Lys Glu Val Ile Leu Thr Pro Thr His Leu Ala Ile Val Met Glu Tyr
                85                  90                  95

Ala Ser Gly Gly Glu Leu Phe Glu Arg Ile Cys Asn Ala Gly Arg Phe
            100                 105                 110

Ser Glu Asp Glu Ala Arg Phe Phe Gln Gln Leu Ile Ser Gly Val
        115                 120                 125

Ser Tyr Cys His Ala Met Gln Val Cys His Arg Asp Leu Lys Leu Glu
    130                 135                 140

Asn Thr Leu Leu Asp Gly Ser Pro Ala Pro Arg Leu Lys Ile Cys Asp
145                 150                 155                 160

Phe Gly Tyr Ser Lys Ser Ser Val Leu His Ser Gln Pro Lys Ser Thr
                165                 170                 175

Val Gly Thr Pro Ala Tyr Ile Ala Pro Glu Val Leu Leu Lys Lys Glu
            180                 185                 190

Tyr Asp Gly Lys Val Ala Asp Val Trp Ser Cys Gly Val Thr Leu Tyr
        195                 200                 205

Val Met Leu Val Gly Ala Tyr Pro Phe Glu Asp Pro Glu Glu Pro Lys
    210                 215                 220
```

```
Asn Phe Arg Lys Thr Ile His Arg Ile Leu Asn Val Gln Tyr Ala Ile
225                 230                 235                 240

Pro Asp Tyr Val His Ile Ser Pro Glu Cys Arg His Leu Ile Ser Arg
            245                 250                 255

Ile Phe Val Ala Asp Pro Ala Lys Arg Ile Ser Ile Pro Glu Ile Arg
        260                 265                 270

Asn His Glu Trp Phe Leu Lys Asn Leu Pro Ala Asp Leu Met Asn Asp
    275                 280                 285

Asn Thr Met Thr Thr Gln Phe Asp Glu Ser Asp Gln Pro Gly Gln Ser
290                 295                 300

Ile Glu Glu Ile Met Gln Ile Ile Ala Glu Ala Thr Val Pro Pro Ala
305                 310                 315                 320

Gly Thr Gln Asn Leu Asn His Tyr Leu Thr Gly Ser Leu Asp Ile Asp
            325                 330                 335

Asp Asp Met Glu Glu Asp Leu Glu Ser Asp Leu Asp Asp Leu Asp Ile
        340                 345                 350

Asp Ser Ser Gly Glu Ile Val Tyr Ala Met
    355                 360

<210> SEQ ID NO 5
<211> LENGTH: 1157
<212> TYPE: DNA
<213> ORGANISM: Artificial Sequence
<220> FEATURE:
<223> OTHER INFORMATION: Synthetic Construct - Plant Optimized sequence
      SnRK2-6 hv6 with appropriate 5' and 3' flanking sequences
<220> FEATURE:
<221> NAME/KEY: CDS
<222> LOCATION: (35)..(1120)

<400> SEQUENCE: 5
gaagacgtgt acagtagtta gttgacacga cacc atg gat cgc cca gct gtt tcc      55
                                     Met Asp Arg Pro Ala Val Ser
                                     1               5 ggt cca atg gac ttg ccc atc atg cat gac tct gac aga tat gaa ctt       103
Gly Pro Met Asp Leu Pro Ile Met His Asp Ser Asp Arg Tyr Glu Leu
        10                  15                  20 gtc aag gac att ggc tcc ggc aac ttt ggt gtt gcc aga ttg atg agg       151
Val Lys Asp Ile Gly Ser Gly Asn Phe Gly Val Ala Arg Leu Met Arg
    25                  30                  35 gac aag caa agc aac gag ctt gtt gct gtc aag tac att gag agg ggt       199
Asp Lys Gln Ser Asn Glu Leu Val Ala Val Lys Tyr Ile Glu Arg Gly
40                  45                  50                  55 gag aag ata gat gag aat gtg aaa cgt gag atc atc aac cac cgc tcc       247
Glu Lys Ile Asp Glu Asn Val Lys Arg Glu Ile Ile Asn His Arg Ser
                60                  65                  70 ctc cgt cat ccc aac ata gtg cgc ttc aaa gag gtc atc ctc act ccc       295
Leu Arg His Pro Asn Ile Val Arg Phe Lys Glu Val Ile Leu Thr Pro
            75                  80                  85 acc cac ctc gcc att gtc atg gag tat gca tct ggg gga gaa ctc ttc       343
Thr His Leu Ala Ile Val Met Glu Tyr Ala Ser Gly Gly Glu Leu Phe
        90                  95                  100 gag agg atc tgc aat gct ggg agg ttc tca gaa gat gag gca agg ttc       391
Glu Arg Ile Cys Asn Ala Gly Arg Phe Ser Glu Asp Glu Ala Arg Phe
    105                 110                 115 ttt ttc cag caa ctc atc tct gga gtc agc tac tgc cat gca atg caa       439
Phe Phe Gln Gln Leu Ile Ser Gly Val Ser Tyr Cys His Ala Met Gln
120                 125                 130                 135
```

```
gtg tgc cac cgt gac ttg aag ttg gaa aac aca ctt ttg gat ggt tct    487
Val Cys His Arg Asp Leu Lys Leu Glu Asn Thr Leu Leu Asp Gly Ser
            140                 145                 150 cca gcc cct cgt ctc aag atc tgt gac ttt ggc tac tcc aaa tca tct    535
Pro Ala Pro Arg Leu Lys Ile Cys Asp Phe Gly Tyr Ser Lys Ser Ser
        155                 160                 165 gtg ctt cac tcc cag cca aag tca aca gtg gga act cca gca tac atc    583
Val Leu His Ser Gln Pro Lys Ser Thr Val Gly Thr Pro Ala Tyr Ile
    170                 175                 180 gct ccc gag gtc ctc ttg aag aaa gag tat gat gga aag gtg gct gat    631
Ala Pro Glu Val Leu Leu Lys Lys Glu Tyr Asp Gly Lys Val Ala Asp
185                 190                 195 gtt tgg tct tgt ggg gtg acc ctc tat gtc atg ctt gtg gga gcc tac    679
Val Trp Ser Cys Gly Val Thr Leu Tyr Val Met Leu Val Gly Ala Tyr
200                 205                 210                 215 cct ttt gaa gat cct gaa gag cca aag aat ttc cgc aaa acc atc cac    727
Pro Phe Glu Asp Pro Glu Glu Pro Lys Asn Phe Arg Lys Thr Ile His
                220                 225                 230 aga atc ctt aat gtt caa tat gcc att cca gat tac gtt cac ata tct    775
Arg Ile Leu Asn Val Gln Tyr Ala Ile Pro Asp Tyr Val His Ile Ser
            235                 240                 245 ccc gaa tgc aga cac ttg atc tcc aga atc ttt gtt gct gac cca gca    823
Pro Glu Cys Arg His Leu Ile Ser Arg Ile Phe Val Ala Asp Pro Ala
        250                 255                 260 aag aga ata tca att cct gag att agg aat cat gaa tgg ttc ttg aag    871
Lys Arg Ile Ser Ile Pro Glu Ile Arg Asn His Glu Trp Phe Leu Lys
    265                 270                 275 aac ctt cct gcc gac ctc atg aat gac aac aca atg acc act cag ttc    919
Asn Leu Pro Ala Asp Leu Met Asn Asp Asn Thr Met Thr Thr Gln Phe
280                 285                 290                 295 gat gaa tct gat caa cct ggc cag agc ata gag gaa atc atg cag atc    967
Asp Glu Ser Asp Gln Pro Gly Gln Ser Ile Glu Glu Ile Met Gln Ile
                300                 305                 310 att gct gag gca act gtt cct cca gct ggc aca cag aac ttg aac cat    1015
Ile Ala Glu Ala Thr Val Pro Pro Ala Gly Thr Gln Asn Leu Asn His
            315                 320                 325 tac ctc acc ggc agc ttg gac att gat gat gac atg gag gaa gat ctt    1063
Tyr Leu Thr Gly Ser Leu Asp Ile Asp Asp Asp Met Glu Glu Asp Leu
        330                 335                 340 gag agc gac ctt gat gac ctt gac att gac tcc agc ggt gag att gtg    1111
Glu Ser Asp Leu Asp Asp Leu Asp Ile Asp Ser Ser Gly Glu Ile Val
    345                 350                 355 tac gcc atg tgagtagtta gcttaatcac ctagagctcg gtcacca              1157
Tyr Ala Met
360

<210> SEQ ID NO 6
<211> LENGTH: 362
<212> TYPE: PRT
<213> ORGANISM: Artificial Sequence
<220> FEATURE:
<223> OTHER INFORMATION: Synthetic Construct

<400> SEQUENCE: 6

Met Asp Arg Pro Ala Val Ser Gly Pro Met Asp Leu Pro Ile Met His
1               5                   10                  15

Asp Ser Asp Arg Tyr Glu Leu Val Lys Asp Ile Gly Ser Gly Asn Phe
            20                  25                  30

Gly Val Ala Arg Leu Met Arg Asp Lys Gln Ser Asn Glu Leu Val Ala
        35                  40                  45
```

```
Val Lys Tyr Ile Glu Arg Gly Glu Lys Ile Asp Glu Asn Val Lys Arg
 50                  55                  60

Glu Ile Ile Asn His Arg Ser Leu Arg His Pro Asn Ile Val Arg Phe
 65                  70                  75                  80

Lys Glu Val Ile Leu Thr Pro Thr His Leu Ala Ile Val Met Glu Tyr
                 85                  90                  95

Ala Ser Gly Gly Glu Leu Phe Glu Arg Ile Cys Asn Ala Gly Arg Phe
                100                 105                 110

Ser Glu Asp Glu Ala Arg Phe Phe Phe Gln Gln Leu Ile Ser Gly Val
                115                 120                 125

Ser Tyr Cys His Ala Met Gln Val Cys His Arg Asp Leu Lys Leu Glu
130                 135                 140

Asn Thr Leu Leu Asp Gly Ser Pro Ala Pro Arg Leu Lys Ile Cys Asp
145                 150                 155                 160

Phe Gly Tyr Ser Lys Ser Ser Val Leu His Ser Gln Pro Lys Ser Thr
                165                 170                 175

Val Gly Thr Pro Ala Tyr Ile Ala Pro Glu Val Leu Leu Lys Lys Glu
                180                 185                 190

Tyr Asp Gly Lys Val Ala Asp Val Trp Ser Cys Gly Val Thr Leu Tyr
                195                 200                 205

Val Met Leu Val Gly Ala Tyr Pro Phe Glu Asp Pro Glu Glu Pro Lys
210                 215                 220

Asn Phe Arg Lys Thr Ile His Arg Ile Leu Asn Val Gln Tyr Ala Ile
225                 230                 235                 240

Pro Asp Tyr Val His Ile Ser Pro Glu Cys Arg His Leu Ile Ser Arg
                245                 250                 255

Ile Phe Val Ala Asp Pro Ala Lys Arg Ile Ser Ile Pro Glu Ile Arg
                260                 265                 270

Asn His Glu Trp Phe Leu Lys Asn Leu Pro Ala Asp Leu Met Asn Asp
                275                 280                 285

Asn Thr Met Thr Thr Gln Phe Asp Glu Ser Asp Gln Pro Gly Gln Ser
290                 295                 300

Ile Glu Glu Ile Met Gln Ile Ile Ala Glu Ala Thr Val Pro Pro Ala
305                 310                 315                 320

Gly Thr Gln Asn Leu Asn His Tyr Leu Thr Gly Ser Leu Asp Ile Asp
                325                 330                 335

Asp Asp Met Glu Glu Asp Leu Glu Ser Asp Leu Asp Leu Asp Ile
                340                 345                 350

Asp Ser Ser Gly Glu Ile Val Tyr Ala Met
                355                 360

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
tggttcacgt agtgggccat cg                                          22

<210> SEQ ID NO 8
<211> LENGTH: 22
<212> TYPE: DNA
<213> ORGANISM: Artificial Sequence
<220> FEATURE:
<223> OTHER INFORMATION: Primer
```

<400> SEQUENCE: 8
tcttggttcc ggtaactttg ga                                    22

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ccaacgacga cttctttctt                                       20

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
ttggtcaatt gcgtagataa ag                                    22

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
gcaaagcagc ttcccaagaa ga                                    22

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
ctccgctact gtcaatgtcg at                                    22

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
gcagtgagtg gtccaatgga tt                                    22

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
gctcaagaag caaatcttcc aatc                                  24

```
<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
tctcgcttgc tgttactcgc tt                                              22

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
ccttaaaacc aggcagccac ta                                              22

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
atcacaggga cagttcttct cg                                              22

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
tcaggcacca ttttctcctt cc                                              22

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
ccgaatcctc ccaatttgtc tg                                              22

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
agaaaccaaa tccaaccaac ga                                              22

<210> SEQ ID NO 21
<211> LENGTH: 22
<212> TYPE: DNA
<213> ORGANISM: Artificial Sequence
<220> FEATURE:
<223> OTHER INFORMATION: Primer
```

```
<400> SEQUENCE: 21
cccaacgcca atacaattca tg                                          22

<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
tttctccagc tctggtctga gttc                                        24

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
gaagaagcag gatcagagca atca                                        24

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
gttgtttcct tgccatttcc aa                                          22

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
gtaagctcat ctttctcacc ctgc                                        24

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
tcggagacag caagtgaaac g                                           21

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
ttttgaacat cgaaaccgag a                                           21
```

```
<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
gaagacttgg cgctacttgg aa                                              22

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
ccgctactgt cgatgtcaag a                                               21

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
atgccagaga tcgagattgc c                                               21

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
tggtgaagga tttaggattt gg                                              22

<210> SEQ ID NO 32
<211> LENGTH: 22
<212> TYPE: DNA
<213> ORGANISM: Artificial Sequence
<220> FEATURE:
<223> OTHER INFORMATION: Primer

<400> SEQUENCE: 32
ttatctgatc caagcgattc ga                                              22

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
atggaggaag aacggcgagt tc                                              22

<210> SEQ ID NO 34
<211> LENGTH: 22
<212> TYPE: DNA
<213> ORGANISM: Artificial Sequence
<220> FEATURE:
<223> OTHER INFORMATION: Primer
```

<400> SEQUENCE: 34
gatgatgagc ccagctcatt ca					22

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
ggtgataaag ggaatgcgtg tt					22

<210> SEQ ID NO 36
<211> LENGTH: 22
<212> TYPE: DNA
<213> ORGANISM: Artificial Sequence
<220> FEATURE:
<223> OTHER INFORMATION: Primer

<400> SEQUENCE: 36
aaccggttgg ttaatcaaac ga					22

<210> SEQ ID NO 37
<211> LENGTH: 22
<212> TYPE: DNA
<213> ORGANISM: Artificial Sequence
<220> FEATURE:
<223> OTHER INFORMATION: Primer

<400> SEQUENCE: 37
tggccgaaga ctctaattct tc					22

<210> SEQ ID NO 38
<211> LENGTH: 22
<212> TYPE: DNA
<213> ORGANISM: Artificial Sequence
<220> FEATURE:
<223> OTHER INFORMATION: Primer

<400> SEQUENCE: 38
tatgattatc accgtgccac ga					22

<210> SEQ ID NO 39
<211> LENGTH: 30
<212> TYPE: DNA
<213> ORGANISM: Artificial Sequence
<220> FEATURE:
<223> OTHER INFORMATION: Primer

<400> SEQUENCE: 39
tgaggtctac aggccaaatt cgctcttagc				30

<210> SEQ ID NO 40
<211> LENGTH: 23
<212> TYPE: DNA
<213> ORGANISM: Artificial Sequence
<220> FEATURE:
<223> OTHER INFORMATION: Primer

<400> SEQUENCE: 40
atcacattgc gtacacaatc tct					23

```
<210> SEQ ID NO 41
<211> LENGTH: 26
<212> TYPE: DNA
<213> ORGANISM: Artificial Sequence
<220> FEATURE:
<223> OTHER INFORMATION: Primer

<400> SEQUENCE: 41
gtgacccggt cgtgccctc tctaga                                              26

<210> SEQ ID NO 42
<211> LENGTH: 26
<212> TYPE: DNA
<213> ORGANISM: Artificial Sequence
<220> FEATURE:
<223> OTHER INFORMATION: Primer

<400> SEQUENCE: 42
ccgtggatat atgccgtgaa caattg                                             26

<210> SEQ ID NO 43
<211> LENGTH: 30
<212> TYPE: PRT
<213> ORGANISM: Artificial Sequence
<220> FEATURE:
<223> OTHER INFORMATION: Positions from 137 to 166 in the kinase domain
      of SnRK2 6 protein

<400> SEQUENCE: 43

Cys His Arg Asp Leu Lys Leu Glu Asn Thr Leu Leu Asp Gly Ser Pro
1               5                   10                  15

Ala Pro Arg Leu Lys Ile Cys Asp Phe Gly Tyr Ser Lys Ser
            20                  25                  30

<210> SEQ ID NO 44
<211> LENGTH: 22
<212> TYPE: PRT
<213> ORGANISM: Artificial Sequence
<220> FEATURE:
<223> OTHER INFORMATION: Positions from 286 to 307 in the regulatory
      domain of SnRK2 6 protein

<400> SEQUENCE: 44

Met Asn Asp Asn Thr Met Thr Thr Gln Phe Asp Glu Ser Asp Gln Pro
1               5                   10                  15

Gly Gln Ser Ile Glu Glu
            20
```